(12) United States Patent
Ollier et al.

(10) Patent No.: US 9,340,410 B2
(45) Date of Patent: May 17, 2016

(54) DEVICE COMPRISING A FLUID CHANNEL FITTED WITH AT LEAST ONE MICROELECTRONIC OR NANOELECTRONIC SYSTEM, AND METHOD FOR MANUFACTURING SUCH A DEVICE

(71) Applicant: COMMISSARIAT A L'ENERGIE ATOMIQUE ET AUX ENE ALT, Paris (FR)

(72) Inventors: Eric Ollier, Grenoble (FR); Carine Marcoux, Voiron (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 14/336,351

(22) Filed: Jul. 21, 2014

(65) Prior Publication Data

US 2015/0021720 A1     Jan. 22, 2015

(30) Foreign Application Priority Data

Jul. 22, 2013   (FR) ..................................... 13 57200

(51) Int. Cl.
*B81B 7/00* (2006.01)
*B81C 1/00* (2006.01)
*G01N 30/60* (2006.01)

(52) U.S. Cl.
CPC ............... *B81B 7/0061* (2013.01); *B81B 7/007* (2013.01); *B81C 1/00269* (2013.01); *B81C 1/00309* (2013.01); *G01N 30/6095* (2013.01); *B81B 2201/0214* (2013.01);
(Continued)

(58) Field of Classification Search
CPC ................. B81B 7/0061; B81B 7/007; B81B 2201/0292; B81B 2201/0214; B81B 2201/058; B81B 2207/07; B81B 2207/096; B81C 1/00269; B81C 1/00309; B81C 2203/0118; G01N 30/6095
See application file for complete search history.

(56) References Cited

U.S. PATENT DOCUMENTS 6,548,895 B1    4/2003   Benavides et al.
6,821,819 B1   11/2004   Benavides et al.
(Continued)

FOREIGN PATENT DOCUMENTS

WO   WO 2011/154363 A2   12/2011

OTHER PUBLICATIONS

U.S. Appl. No. 14/182,659, filed Feb. 18, 2014, Ollier.
(Continued)

*Primary Examiner* — Peter Bradford
(74) *Attorney, Agent, or Firm* — Oblon, McClelland, Maier & Neustadt, L.L.P.

(57) ABSTRACT

A device comprising a substrate comprising at least one microelectronic and/or nanoelectronic structure comprising at least one sensitive portion and one fluid channel (2) defined between said substrate and a cap (6), where said fluid channel (2) comprises at least two apertures to provide a flow in said channel, where said microelectronic and/or nanoelectronic structure is located within the fluid channel, where said cap is assembled with the substrate at an assembly interface, where said device comprises electrical connections between said microelectronic and/or nanoelectronic structure and the exterior of the fluid channel (2), where said electrical connections (8) are formed by vias made through the substrate (4) directly below the microelectronic and/or nanoelectronic structure, and in electrical contact with said microelectronic and/or nanoelectronic structure.

15 Claims, 21 Drawing Sheets

Figure 1:
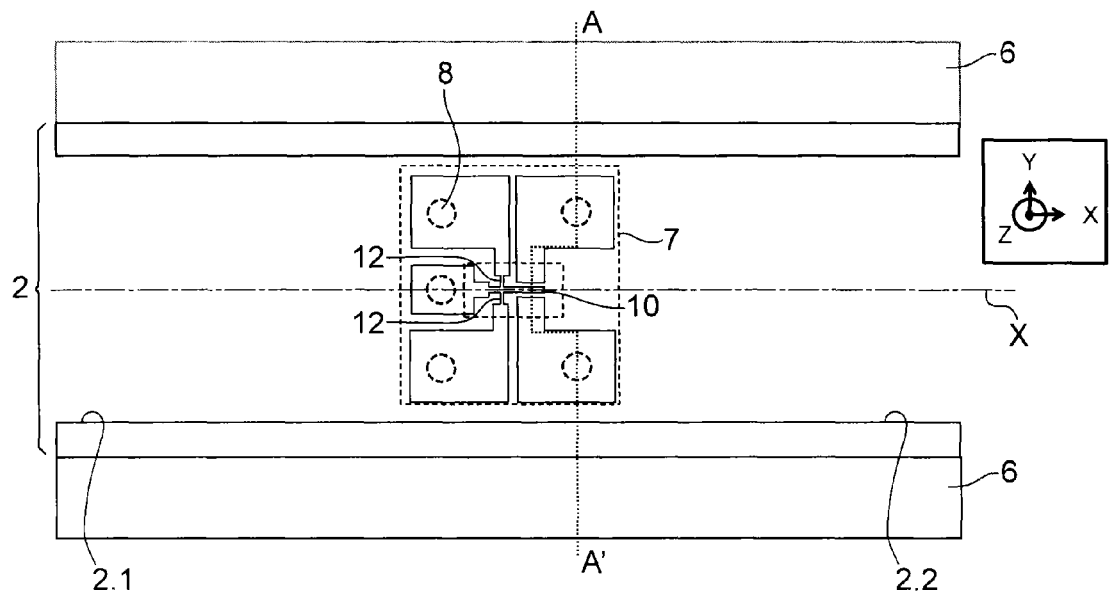

(52) U.S. Cl.
CPC .. *B81B 2201/0292* (2013.01); *B81B 2201/058* (2013.01); *B81B 2207/07* (2013.01); *B81B 2207/096* (2013.01); *B81C 2203/0118* (2013.01)

(56) References Cited

U.S. PATENT DOCUMENTS

| | | | |
|---|---|---|---|
| 7,098,117 | B2 | 8/2006 | Najafi et al. |
| 2007/0013014 | A1* | 1/2007 | Guo et al. ............... 257/417 |
| 2008/0283991 | A1 | 11/2008 | Reinert |
| 2012/0126433 | A1* | 5/2012 | Montanya Silvestre ...... 257/787 |
| 2012/0272742 | A1 | 11/2012 | Andreucci et al. |
| 2013/0144542 | A1 | 6/2013 | Ernst et al. |
| 2013/0214365 | A1* | 8/2013 | Schlarmann ......... G01L 9/0042 257/415 |
| 2014/0158334 | A1 | 6/2014 | Dellea et al. |
| 2014/0162392 | A1 | 6/2014 | Ollier et al. |
| 2014/0166085 | A1 | 6/2014 | Ollier |
| 2014/0264647 | A1* | 9/2014 | Katragadda ......... B81C 1/00238 257/415 |
| 2015/0001990 | A1 | 1/2015 | Ollier et al. |

OTHER PUBLICATIONS

French Preliminary Search Report issued Feb. 21, 2014 in French Application 13 57200, filed on Jul. 22, 2013 ( with English Translation of categories of Cited Documents).

Mr. Magnus Rimskog et al. "High Density Through Silicon Via (TSV)", Design, Test, Integration and Packaging Mems/Moems, 2008, 4 pages.

U.S. Appl. No. 14/514,703, filed Oct. 15, 2014, Ollier, et al.

U.S. Appl. No. 14/335,175, filed Jul. 18, 2014, Ollier, et al.

European Search Report issued Aug. 20, 2014 in Patent Application No. 14177871.2 (with English translation of categories of cited documents).

S. Nicolas, et al., "3D MEMS High Vacuum Wafer Level Packaging" IEEE $62^{nd}$ Electronic Components and Technology Conference (ECTC), 2012, pp. 370-376.

Jian-Qiang Lu, "3-D Hyperintegration and Packaging Technologies for Micro-Nano Systems" Proceedings of the IEEE, vol. 97, No. 1, Jan. 2009, pp. 18-30.

Chiung-Wen Lin, et al., "Thru-Wafer Interconnect for SOI-MEMS 3D Wafer-Level Hermetic Packaging" The $14^{th}$ International Conference on Solid-State Sensors, Actuators and Microsystems, 2007, pp. 2111-2114.

\* cited by examiner

DEVICE COMPRISING A FLUID CHANNEL FITTED WITH AT LEAST ONE MICROELECTRONIC OR NANOELECTRONIC SYSTEM, AND METHOD FOR MANUFACTURING SUCH A DEVICE

TECHNICAL FIELD AND PRIOR ART

The present invention relates to a device comprising a fluid channel fitted with at least one microelectronic or nanoelectronic system, and to a method for manufacturing such a device.

Microelectronic or nanoelectronic systems comprise MEMS (microelectromechanical systems) and NEMS (manoelectromechanical systems). For the sake of simplification they will be called MEMS and NEMS in the remainder of the description. These systems are now commonly used in many products. New applications are appearing, particularly due to the development of NEMS, which provide new benefits due to their smaller dimensions. In particular, due to the great mass sensitivity of this type of system, they are of great interest for chemical or biological sensors.

An NEMS or an MEMS comprises a stationary portion and at least one sensitive portion, which may possibly be suspended, relative to the stationary portion.

But for these applications in particular the exposure of the MEMS or NEMS type structure, which provides particular physico-chemical characteristics, to a surrounding environment, generally a gaseous or liquid environment, must be managed. To achieve this the sensitive MEMS or NEMS structure is positioned in a fluid channel in which the medium flows, allowing the medium to be analysed to be brought into contact with the sensitive NEMS or MEMS structure.

These sensitive structures are connected to an electronic system for powering and processing the signals by electrical connections, where the latter connect the structure to the electronic system, at least a portion of which is located outside the fluid channel.

The fluid channel is produced by adding a cap to a substrate comprising the sensitive structure or structures. The cap is sealed in a fluid-tight manner on the substrate, and comprises at least two apertures to allow the fluid to be analysed to flow in the channel. The cap has a cavity made in a substrate, which is between several µm and several hundreds of µm deep, for example.

Document WO2011/154363 describes an analysis device, for example a gas chromatography microcolumn comprising MEMS and/or NEMS in the microcolumn, forming sensors. The microcolumn is formed of a substrate and a cap. The MEMS and/or NEMS connection is made, for example, by vias made in the substrate and emerging at the assembly interface between the cap and the substrate. Connection lines connect the vias to the sensitive structures. The presence of these vias at the assembly interface makes the assembly complex and, in addition, the electrical connection of the sensitive structures with the exterior is made complex due to the production of the vias and of the connection lines.

The cap sealing can use techniques of the polymer sealing, molecular sealing, anode sealing, eutectic sealing, glass sintering, etc. types. The problem is then posed of the production of the electrical connections between the sensitive structure or structures located inside the fluid channel and the exterior of the fluid channel since the sealing, whilst allowing these electrical connections, must be fluid-tight.

One technique consists, after the cap has been sealed, in opening broad cavities deep within the cap only above areas of metallised contacts to allow direct contact by wirebonding on these contacts, where each contact contact is surrounded by a sealing bead, for example one made of polymer, to insulate this portion of the cavity. But this technique has the disadvantage that it introduces additional patterns for these electrical passages inside the fluid channel, which is not desirable since they can cause disturbances in the flow of the fluid, dead volumes to be generated, etc. Furthermore, this technique is unsuitable in the case of sensitive structures of the NEMS or MEMS type since these structures require small-size semiconductor material or metal contact contacts to reduce the parasitical capacities and to be able to extract a usable electrical signal with a satisfactory signal-to-noise ratio. Finally, this technique is not suitable for components formed of NEMS or MEMS in networks, since these networks must be interconnected with a high density, which implies the use of very small-size contact contacts, and possibly the use of several metal levels.

Another technique to produce these electrical connections whilst guaranteeing tightness consists in producing connections of the Via type, for example TSVs (Through Silicon Vias) or TGVs (Through Glass Vias). Document "3D MEMS high vacuum wafer level packaging—S. Nicolas et al. Electronic Components and Technology Conference (ECTC), 2012 IEEE 62nd, Date of Conference: May 29, 2012-Jun. 1, 2012, describes such manufacturing. For example, such connections of the TSV type would, for example, be made deep within the cap and would emerge in the cavity, electrical continuity then being provided by a contact/metal bead inside the cavity. And such vias would be made in substantial thicknesses of the semiconductor material, which can be of the order of several hundred µm, making manufacture of small-sized contacts very difficult. In addition, the presence of TSVs traversing the cap and emerging in the fluid cavity can disrupt the operation of the fluid channel, for example by disrupting the propagation of the circulating mixture, by disrupting the chemical properties of the interfaces in contact with the flowing medium due to the materials of the TSVs, etc. In addition, bearing in mind the dimensions of the channel, in particular the height of the cavity, the electrical connection between the TSV in the cap and the sensitive structure would be difficult to make.

DESCRIPTION OF THE INVENTION

One aim of the present invention is consequently to provide a device comprising at least one fluid channel, one or more sensitive structures located in the fluid channel, and electrical connections between the sensitive structure or structures located in the fluid channel and the exterior of the fluid channel which does not have the disadvantages mentioned above.

Another aim is to provide a method for producing such a device with fluid channel.

The aim mentioned above is attained by a structure comprising a substrate, a cap and an assembly interface between the substrate and the cap, a delimited fluid channel between the substrate, the cap and the assembly interface, at least one sensitive structure located in the fluid channel, and at least one electrical connection between the sensitive structure and an area outside the fluid channel, where the electrical connection is formed by a via through the substrate in an area of the fluid channel directly below the microelectronic and/or nanoelectronic structure, outside the sealing interface.

According to the invention, the microelectronic and/or nanoelectronic structure comprises a stationary structure comprising contact contacts, at least one sensitive structure and means of actuation and/or transduction of at least one characteristic of the sensitive structure, where the contact contacts are electrically connected to the sensitive portion and/or to the stationary portion.

The invention simplifies the assembly of the cap and the substrate. In addition, by producing the via directly below the microelectronic and/or nanoelectronic structure this via is in direct contact with the corresponding contact contact. No additional conductive track is required between the via and its contact contact. Furthermore, by positioning the contact in the fluid channel the length of conductive track required between the contact and the sensitive portion, or stationary portion, can be limited, and by this means the quality particularly of the electrical transduction signal can be optimised.

In addition, in the case of a NEMS/MEMS network each of the NEMS/MEMS structures present in the fluid channel can be connected directly and individually, by this means enabling the characteristics of the network to be controlled and optimised.

In addition, the via or vias do not disturb the flow in the channel since they do not emerge into the flow of the fluid; they are concealed underneath the microelectronic and/or nanoelectronic structure. The invention therefore enables the production of vias through the cap and/or the opening of broad cavities deep within the cap to allow contact to be avoided.

In other words, the vias are produced through the substrate directly beneath the microelectronic and/or nanoelectronic structure.

Very advantageously, an intermediate layer can be comprised between the cap and the substrate to facilitate assembly. The intermediate layer can have a surface state allowing sealing with the faces of the base of the cap, for example a dry film sealing, a molecular or eutectic sealing, or a thermocompression sealing. The face fit for sealing can have a certain roughness or a certain relief which nevertheless allows sealing.

In an equally advantageous manner the intermediate layer can be comprised in the fluid channel, the intermediate layer can be such that it encapsulates the materials of the NEMS or MEMS structure, except for the sensitive portion which, due to their presence in the fluid channel, could interact with the medium flowing in the channel, i.e. it isolates the materials of the NEMS or MEMS structure other than the sensitive portion from the interior of the fluid channel. This is the case, for example, with the metals or dielectrics which are used in the fluid channel if the mechanical structure comprises a dense network of NEMS. In this case the intermediate layer is advantageously only open in the NEMS or MEMS structures intended to interact with the surrounding medium.

The sensitive structure can advantageously be functionalised.

In a preferred manner the assembly is produced by means of a dry film; such a method of assembly is particularly suitable if the sensitive structure is functionalised.

Very advantageously, the via(s) is/are produced after the cap is assembled on the substrate, enabling the substrate to be made thinner, and dense vias to be produced, with the cap acting as a handle.

Furthermore, the structure according to the invention and its production method enable collective production of dies having a fluid channel, where the dies are separated by sawing between the channels and by pre-cuts crossways to the channels.

One subject-matter of the present invention is then a device comprising a substrate comprising at least one microelectronic and/or nanoelectronic structure comprising at least one sensitive portion and one fluid channel defined between said substrate and a cap, where said fluid channel comprises at least two apertures to provide a flow in said channel, where said microelectronic and/or nanoelectronic structure is located within the fluid channel, where said cap is assembled with the substrate at an assembly interface, where said device comprises at least one electrical connection between said microelectronic and/or nanoelectronic structure and the exterior of the fluid channel, where the electrical connection is formed by a via made at least partly through the substrate directly below the microelectronic and/or nanoelectronic structure, and in electrical contact with the microelectronic and/or nanoelectronic structure.

The via can be in electrical contact with the microelectronic and/or nanoelectronic structure through a contact contact located in the fluid channel.

The device can very advantageously comprise an intermediate layer located at least partly in the fluid channel, where said intermediate layer covers, in the fluid channel, at least partly the microelectronic and/or nanoelectronic structure, except for its sensitive portion or an intermediate layer located only at the assembly interface located between the cap and the substrate.

The intermediate layer can comprise an electrical insulating material, such as a silicon oxide, or a silicon nitride.

According to an additional characteristic the device can advantageously comprise a functionalisation layer at least partly covering a part of the sensitive portion of the microelectronic and/or nanoelectronic structure.

The device can comprise several microelectronic and/or nanoelectronic structures interconnected in said fluid channel. The microelectronic and/or nanoelectronic structures can be interconnected by interconnection lines located in the fluid channel.

The intermediate layer advantageously electrically insulates the interconnection lines.

In one example embodiment the device comprises a dry sealing film interposed between the substrate and the cap. The dry sealing film can comprise several beads.

In another example embodiment the device comprises at least one layer of material interposed between the substrate and the cap making a eutectic or metallic sealing, or thermocompression sealing, or screen print sealing, or in which the sealing is molecular sealing or glass frit.

The intermediate layer can advantageously comprise at least one first planarising layer and one second layer deposited on the first layer, where said second layer is made of a material such that is not very sensitive, or is insensitive, to a step of release of the microelectronic and/or nanoelectronic structure. The first layer is sufficiently thick to efface the variations of topology, and it is advantageously insulating when the intermediate layer is on the contact contacts of the microelectronic and/or nanoelectronic structure.

The channel can advantageously form a gas chromatography microcolumn.

Another subject-matter of the present invention is a method for manufacturing at least one device according to the invention, comprising the following steps:

a) production of at least one microelectronic and/or nanoelectronic structure on a substrate, b) production of a cap comprising a fluid channel, in a cap substrate c) sealing of the cap and of the substrate such that the microelectronic and/or nanoelectronic structure is located in the fluid channel, d) production of at least one via in the substrate directly below the microelectronic and/or nanoelectronic structure.

Step d) can take place after step c) or before step c).

Production of the via can comprise at least

The step of production of a hole in at least a portion of the substrate

The step of filling all or part of said hole with an electrically conductive material.

The method can comprise, prior to the production of the at least one via, and after step d), a step of thinning of the substrate.

The method can comprise, prior to the step of filling of said hole with an electrically conductive material, a step of deposition on the inner surface of the hole of an electrically insulating material.

For example the hole is produced by deep etching followed by fine etching.

If the sensitive portion of the microelectronic and/or nanoelectronic structure is suspended, where this portion is, for example, released before step c).

The method can also comprise a step of formation of an intermediate layer on the substrate after step a) in an area such that it comprises at least one portion located in the fluid channel after step d) or a step of formation of an intermediate layer on the substrate after step a) in an area such that it is located only at the assembly interface after step d).

The method can comprise, in step a), production in the microelectronic and/or nanoelectronic structure of at least one electrical contact contact intended to provide an electrical contact with the via. The method can then also comprise, to form said contact contact, an additional metal deposition on the contact.

The method can also comprise a step of production of an electrical distribution layer on the face of the device in which said via emerges.

The method preferably comprises a step of production of a functionalisation layer inside the fluid channel on the microelectronic and/or nanoelectronic structure and/or on the walls of the cap and/or on the intermediate layer, where said step is accomplished before sealing.

As a variant, the functionalisation layer can possibly be produced after sealing.

In one example embodiment the sealing step uses a dry film, and the production method then comprises the following sub-steps:

lamination of the dry film on the base faces of the walls of the cap, structuring of the dry film, bringing the cap and the substrate with the microelectronic and/or nanoelectronic structure(s) closer, application of a pressure so as to press the dry film.

In another example embodiment the sealing is an eutectic or metal sealing, thermocompression sealing, or a molecular sealing or screen print sealing.

Several devices can be produced simultaneously; the substrate then comprises several microelectronic and/or nanoelectronic structures and the cap substrate comprises several caps, where the caps are sealed simultaneously on the substrate comprising the microelectronic and/or nanoelectronic structures, such that a fluid channel of a device can or cannot communicate with the fluid channel of other devices.

The method can comprise the following steps:

a step of production of pre-cuts in a direction perpendicular to the fluid channels in the cap substrate and in the substrate, a step of separation of the devices, advantageously by cleavage.

a step of pre-cutting or of cutting in a direction parallel to the fluid channels between the channels, a step of separation of the devices, advantageously by cleavage of the pre-cuts.

BRIEF DESCRIPTION OF THE ILLUSTRATIONS

Figure 2:
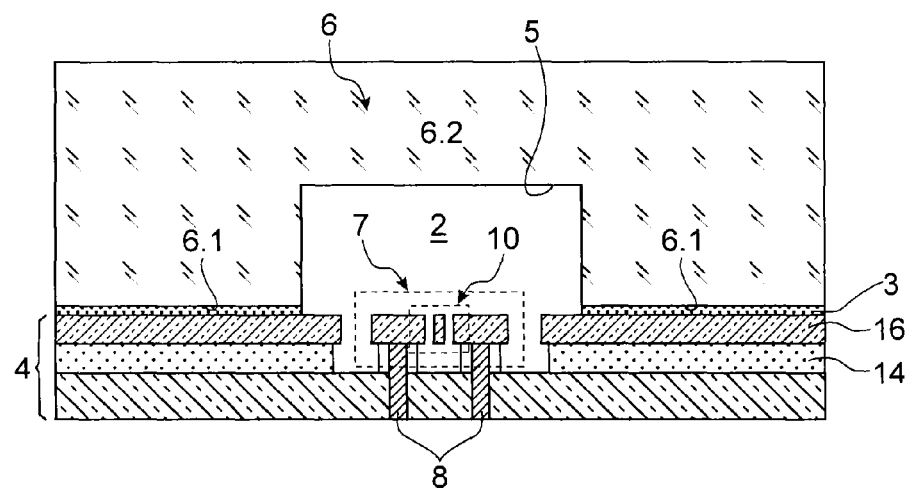
Figure 3:
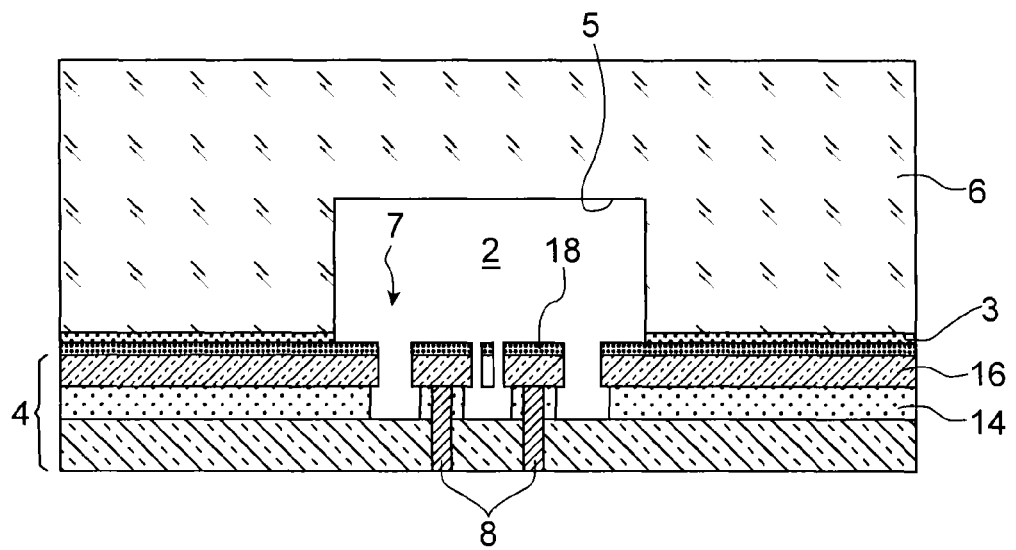
Figure 4:
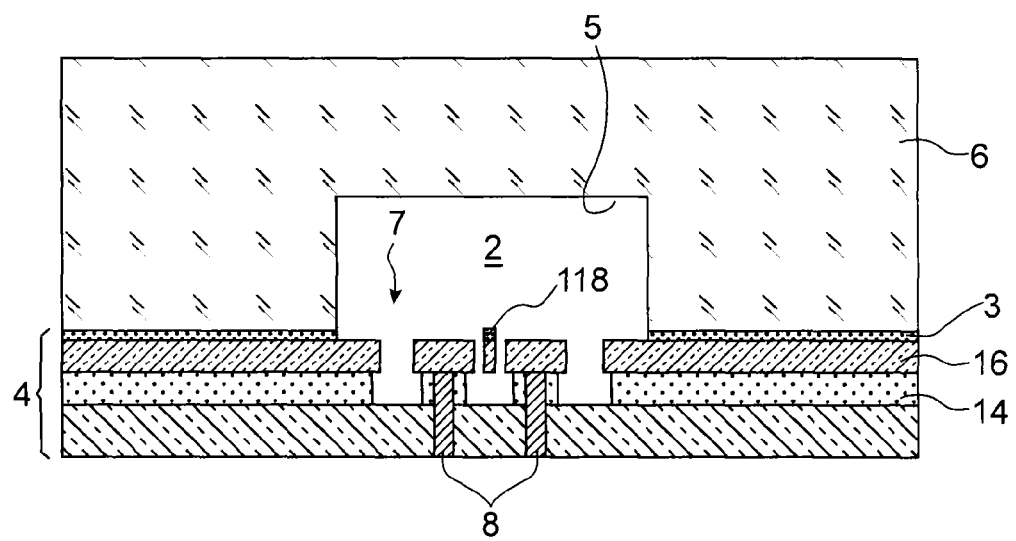
Figure 5A:
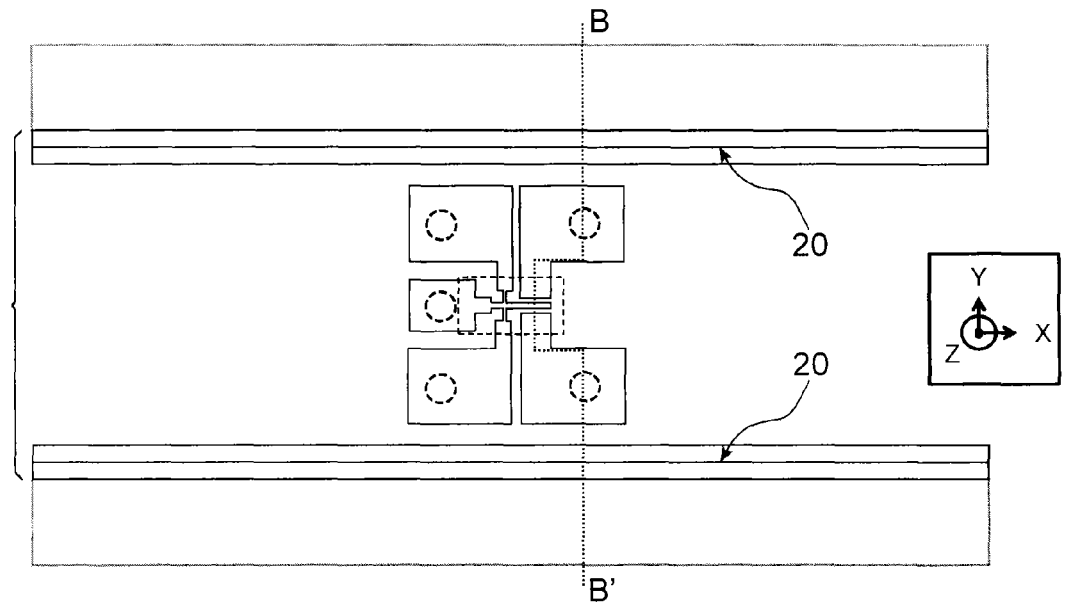
Figure 5B:
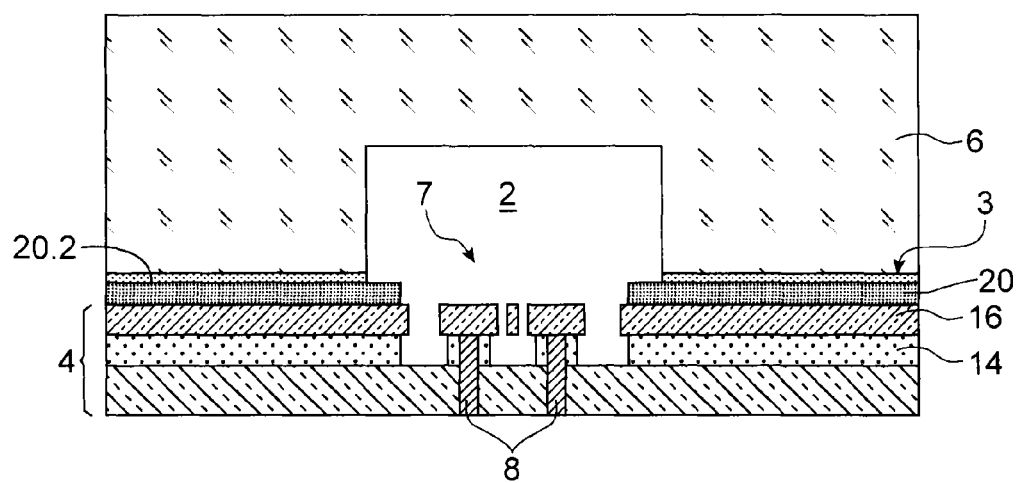
Figure 6:
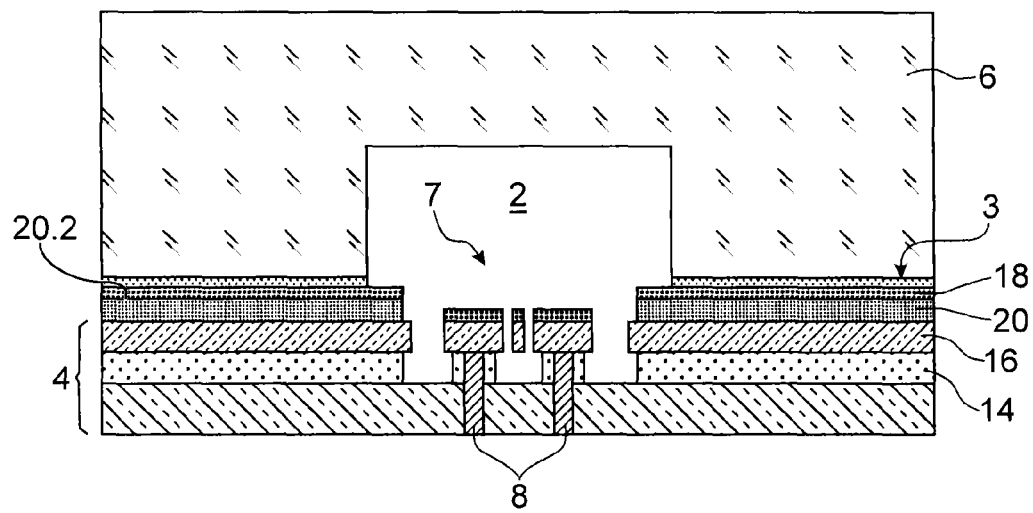
Figure 7:
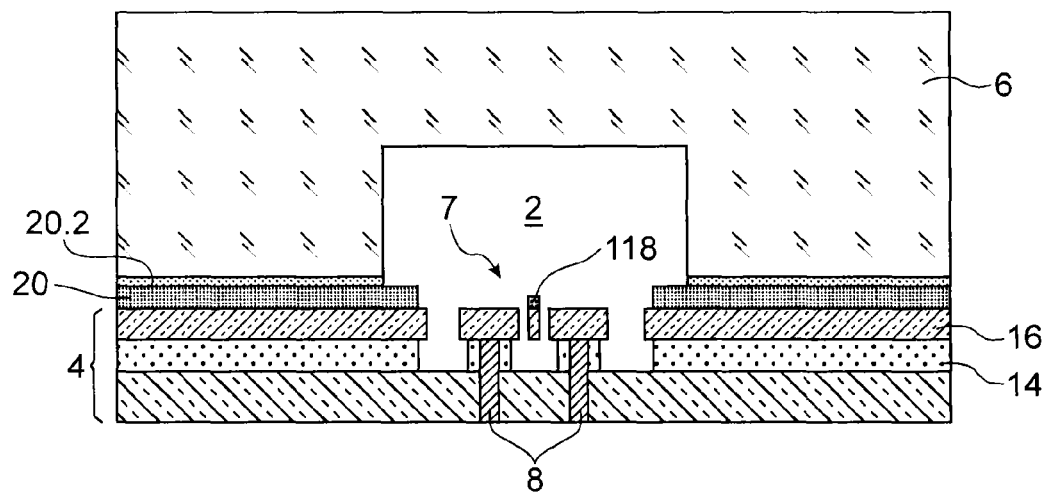
Figure 8A:
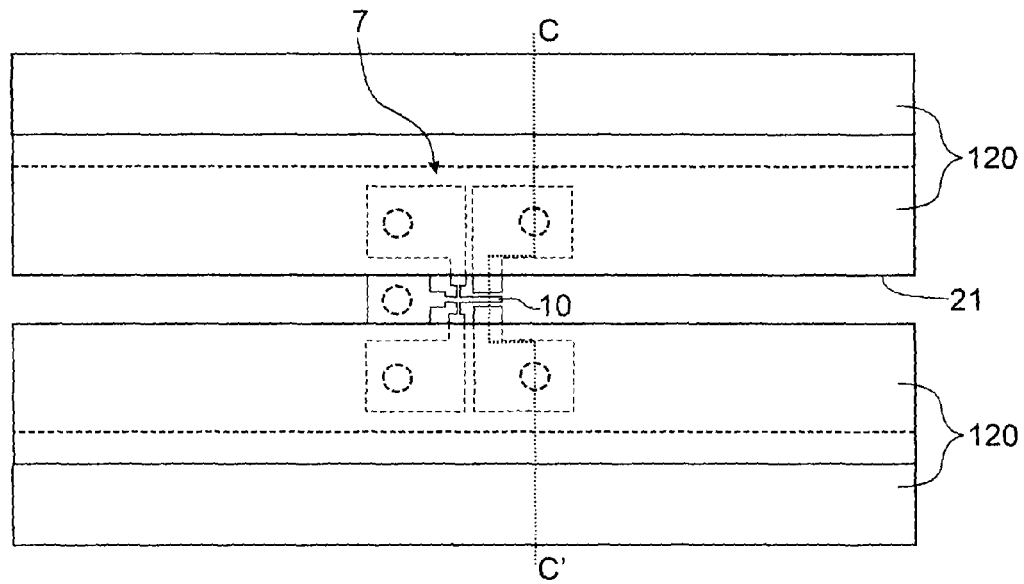
Figure 8B:
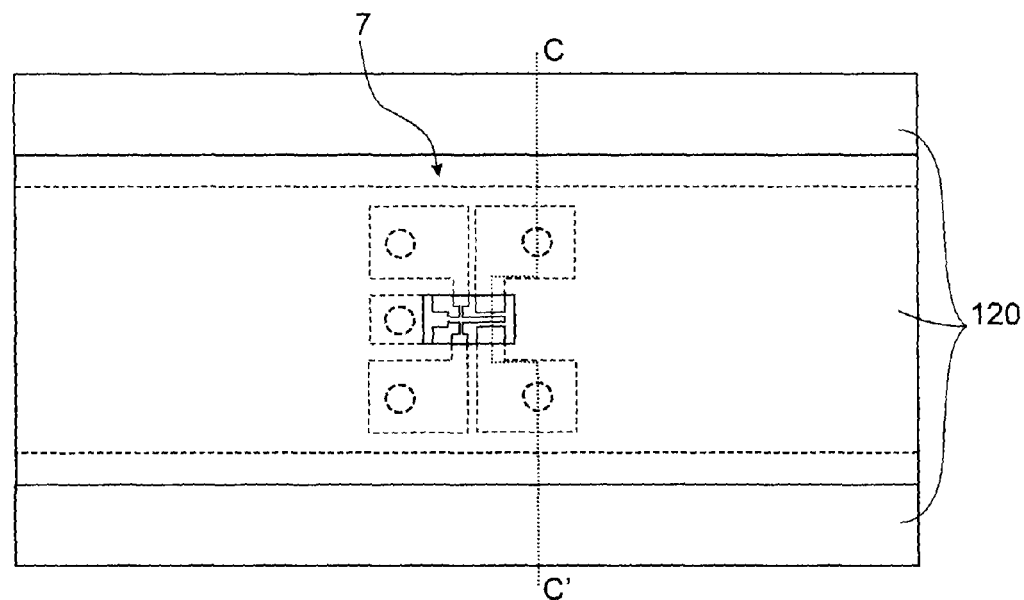
Figure 8C:
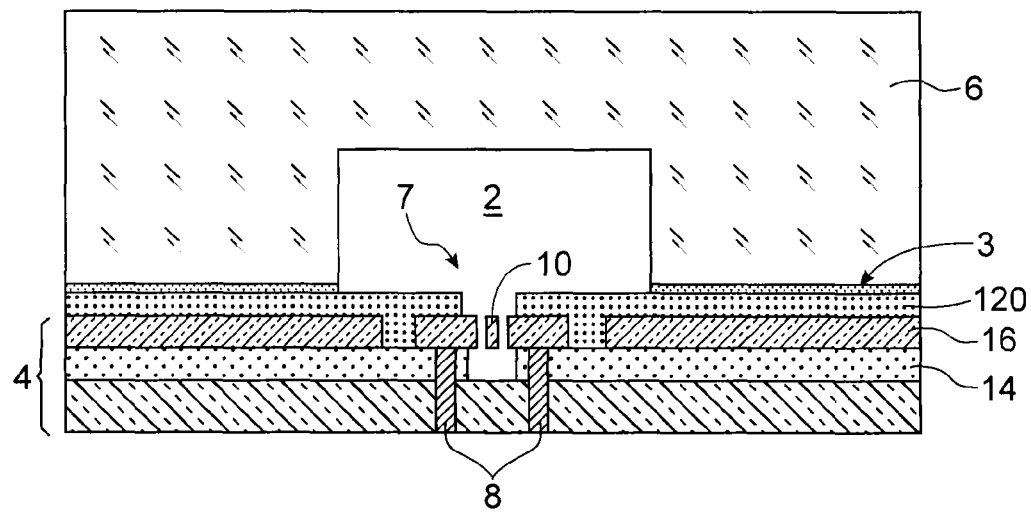
Figure 9:
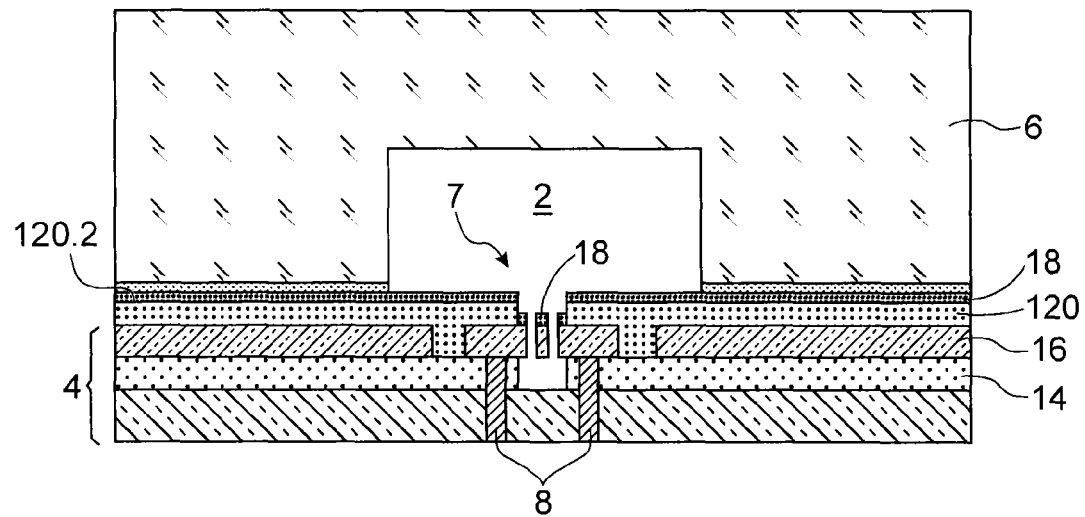
Figure 10:
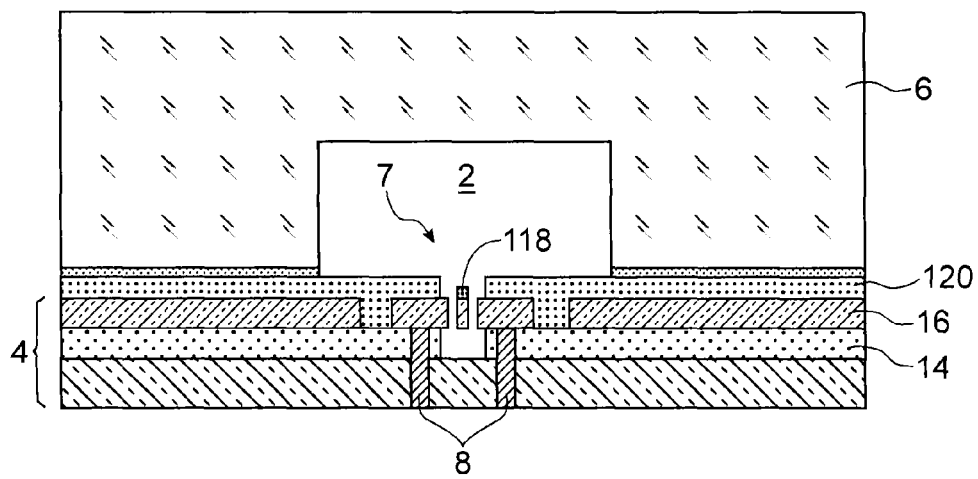
Figure 11A:
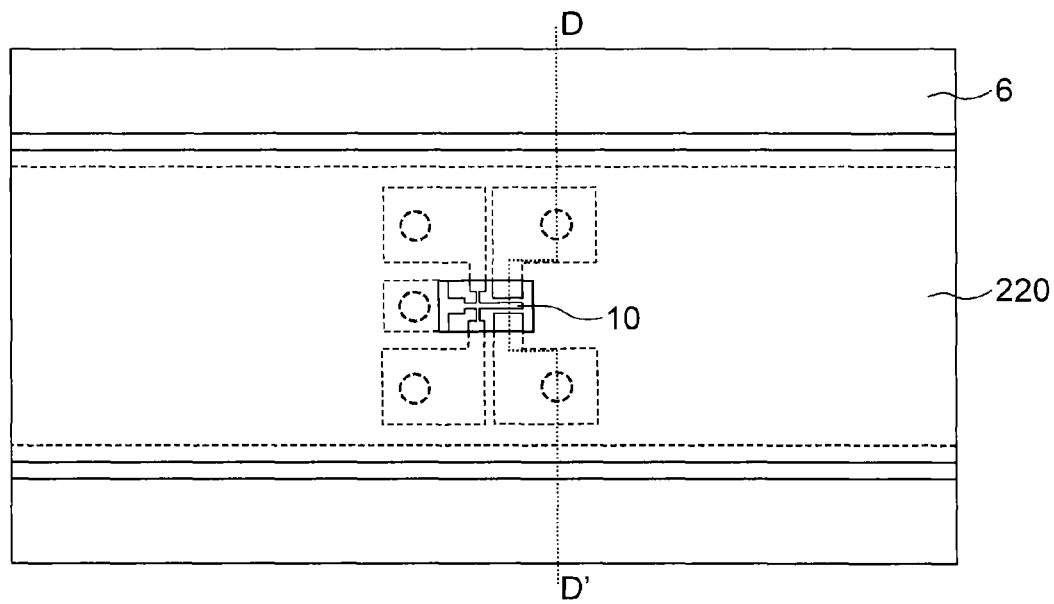
Figure 11B:
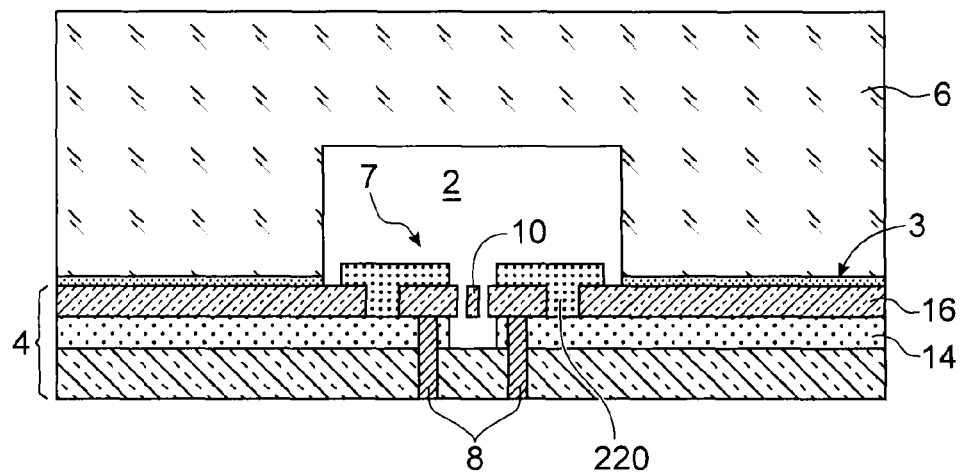
Figure 12A:
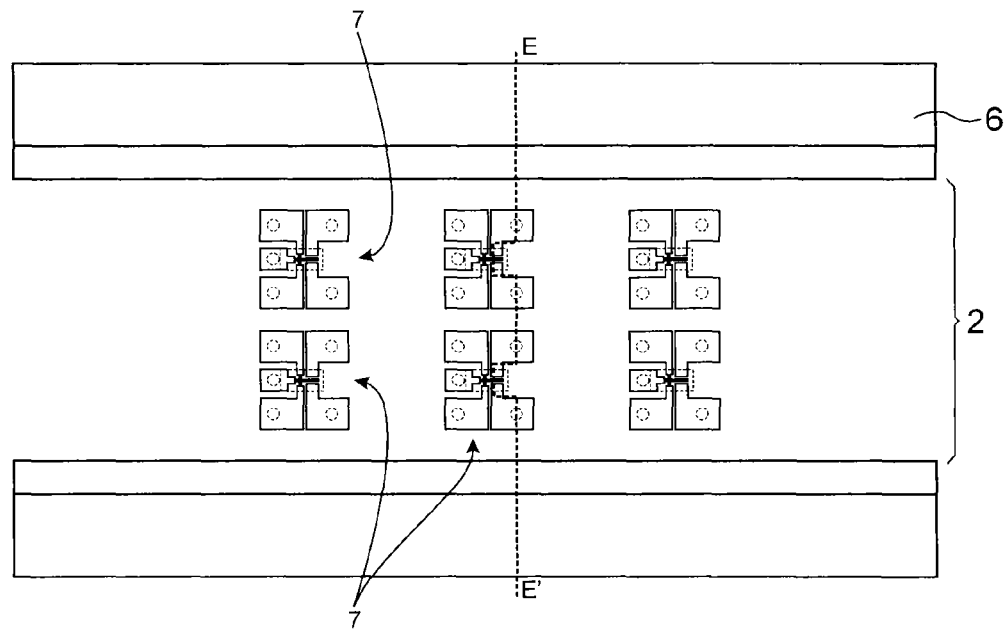
Figure 12B:
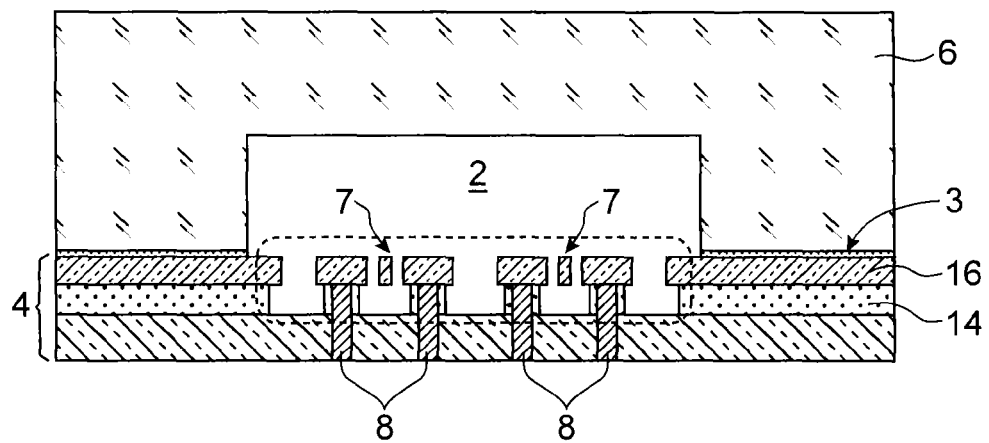
Figure 13A:
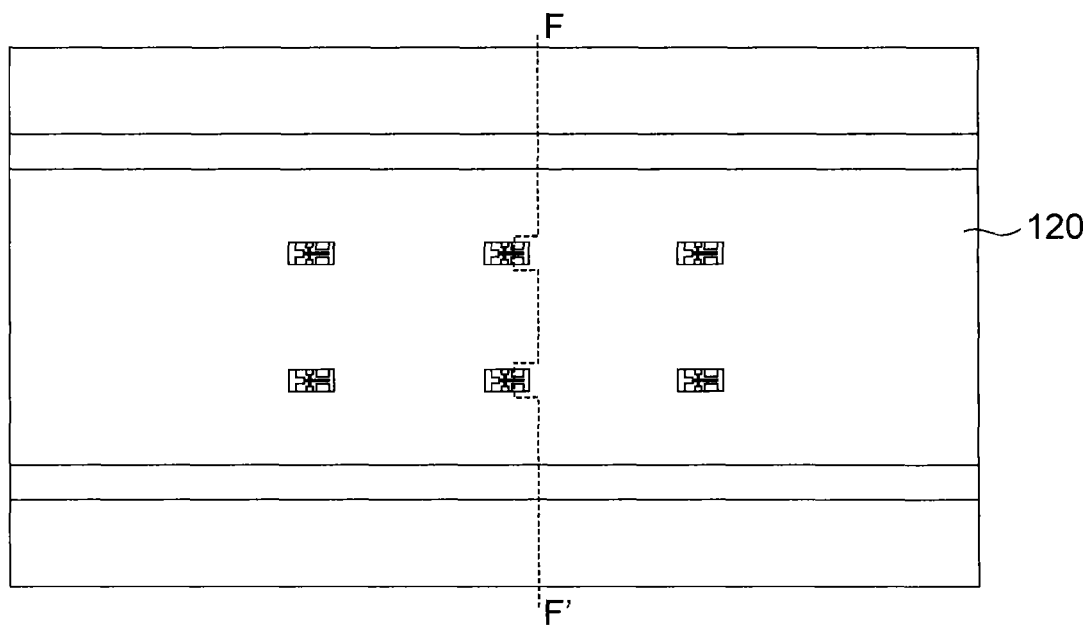
Figure 13B:
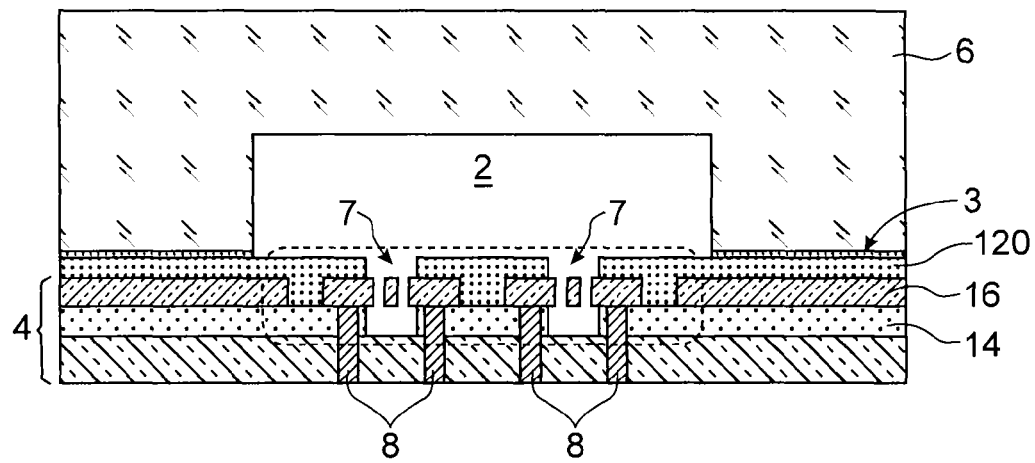
Figure 14:
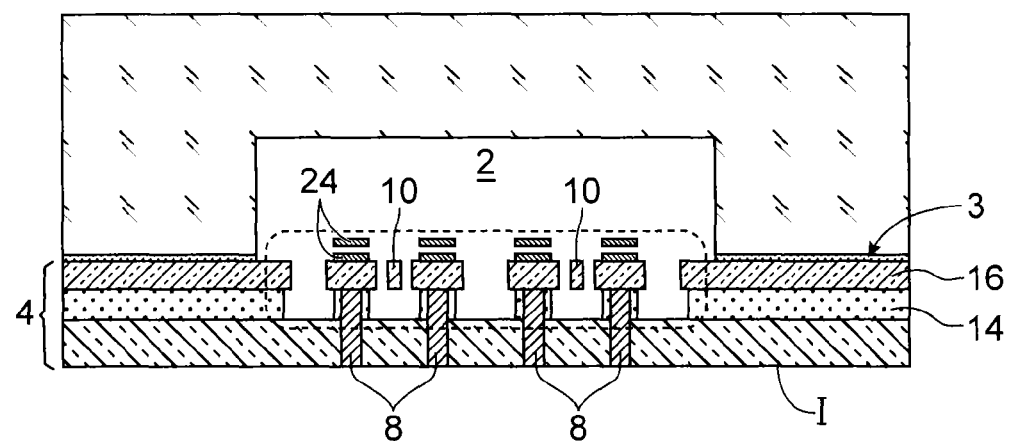
Figure 15:
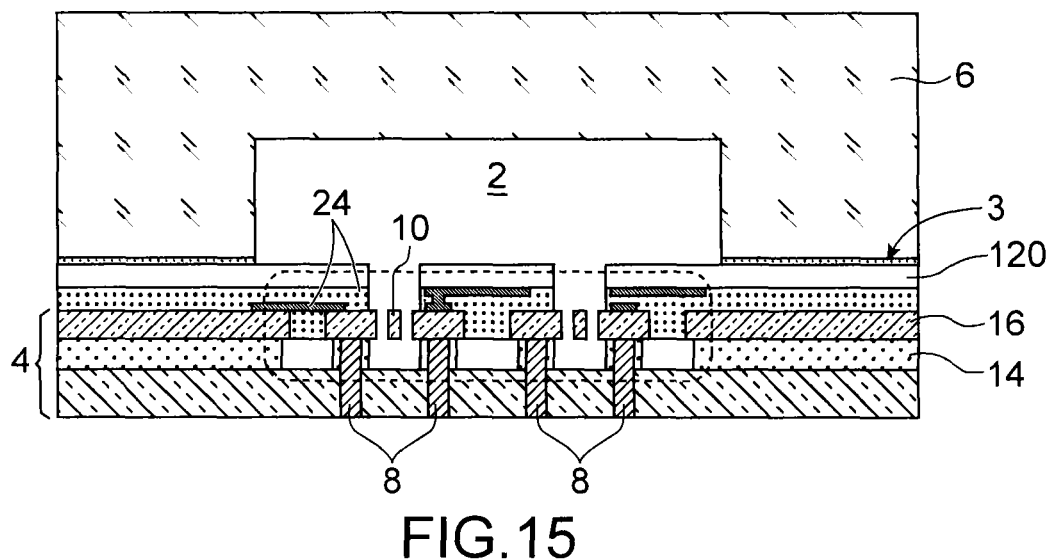
Figure 16:
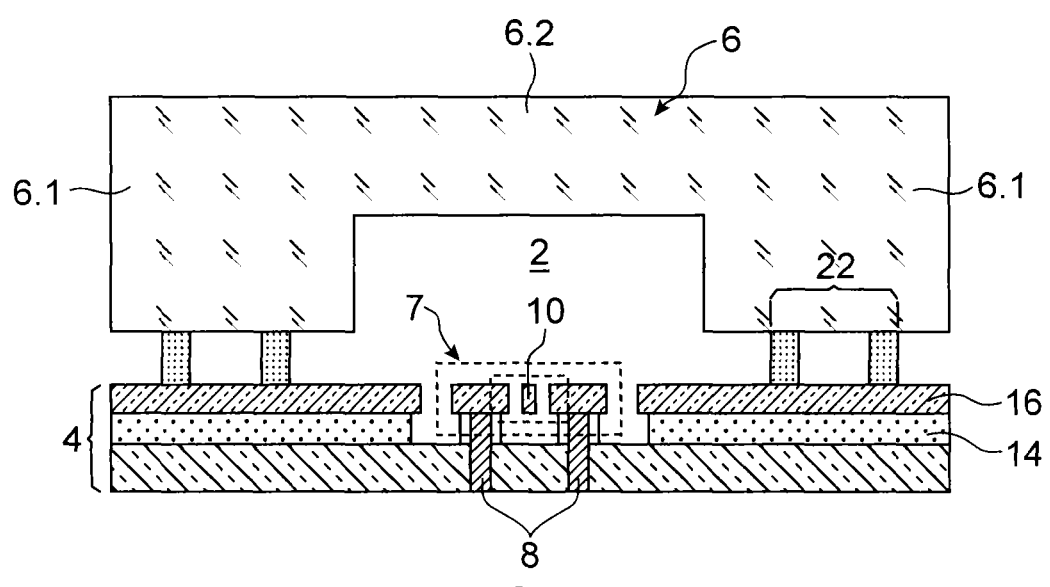
Figure 17:
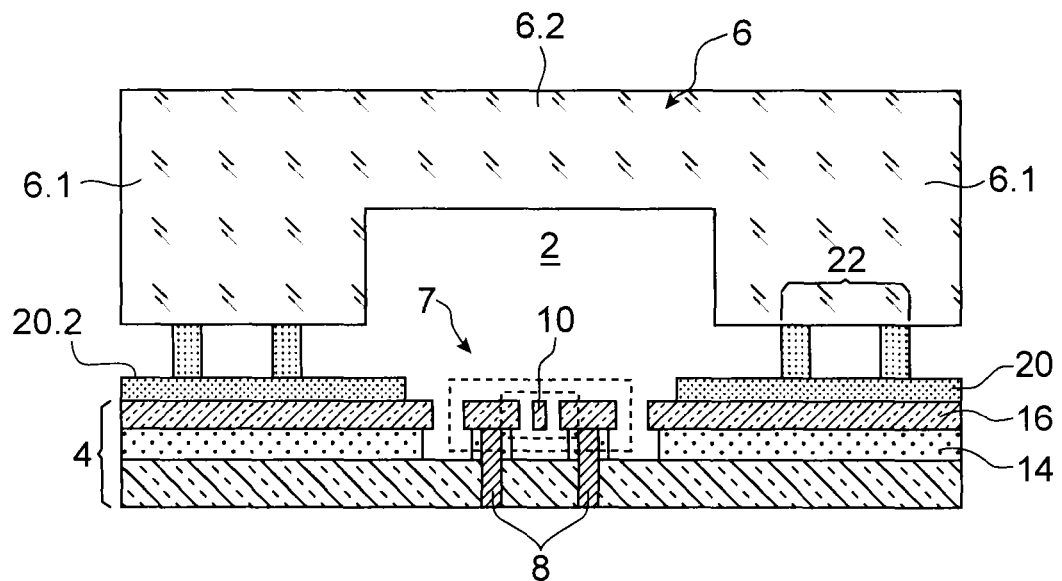
Figure 18:
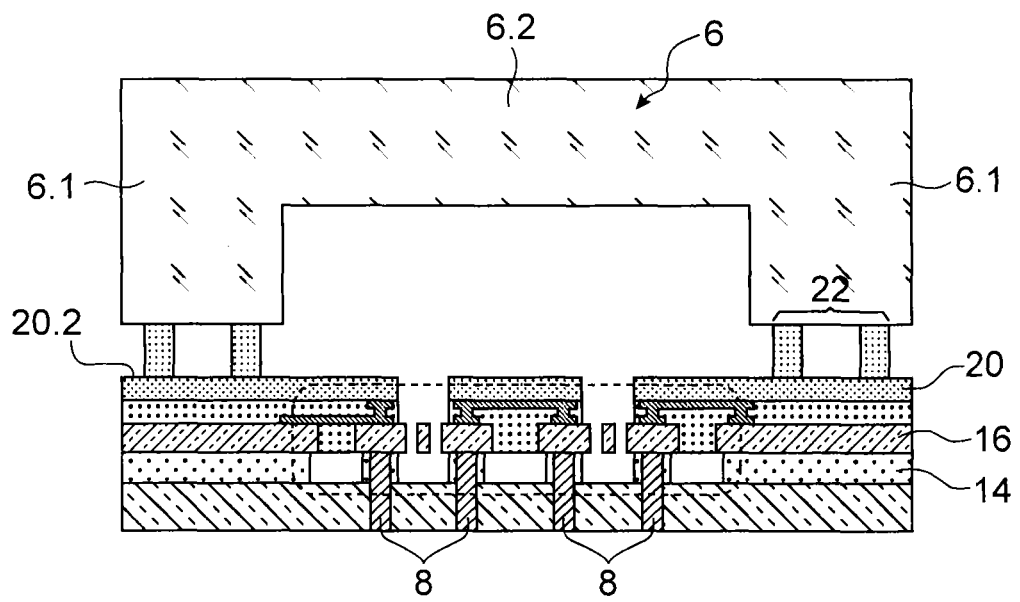

The present invention will be better understood using the description which follows and the appended illustrations, in which:

FIG. 1 is a top view of a device with fluid channel comprising MEMS/NEMS structures according to one example embodiment of the invention, FIG. 2 is a cross-section view of the device of FIG. 1 along plane A-A', FIG. 3 is a cross-section view of a device according to a variant of the device of FIG. 1, in which a non-localised functionalisation layer is implemented, FIG. 4 is a cross-section view of a device according to a variant of the device of FIG. 1, in which a non-localised functionalisation layer is implemented, FIG. 5A is a top view of a device with fluid channel comprising MEMS/NEMS structures according to another example embodiment of the invention implementing an intermediate layer between the cap and the substrate, FIG. 5B is a cross-section view of the device of FIG. 5A along plane B-B', FIG. 6 is a cross-section view of a device according to a variant of the device of FIG. 5A, in which a non-localised functionalisation layer is implemented, FIG. 7 is a cross-section view of a device according to a variant of the device of FIG. 5A, in which a localised functionalisation layer is implemented, FIG. 8A is a top view of a device with fluid channel comprising MEMS/NEMS structures according to another example embodiment of the invention implementing an intermediate layer between the cap and the substrate, extending within the channel, and delimiting a longitudinal area without an intermediate layer, FIG. 8B is a top view of a variant of the device of FIG. 8A, where the interior of the channel, except for the sensitive portion of the MEMS/NEMS structure, is covered by the intermediate layer, FIG. 8C is a cross-section view of the device of FIG. 8A or that of FIG. 8B, along plane CC', FIG. 9 is a section view of a device according to a variant of the device of FIG. 8C, in which a non-localised functionalisation layer is implemented, FIG. 10 is a cross-section view of a device according to a variant of the device of FIG. 8C, in which a localised functionalisation layer is implemented, FIG. 11A is a top view of a device with fluid channel comprising MEMS/NEMS structures according to another example embodiment of the invention implementing an intermediate layer only within the channel, and delimiting a longitudinal area without an intermediate layer, FIG. 11B is a cross-section view of the device of FIG. 11A along plane DD', FIG. 12A is a top view of another example embodiment with a fluid channel according to the invention, in which several MEMS/NEMS structures are produced, FIG. 12B is a cross-section view of the device of FIG. 12A along plane EE', FIG. 13A is a top view of a variant of the device with fluid channel of FIG. 12A, in which an intermediate layer is formed between the substrate and the cap and within the channel, FIG. 13B is a cross-section view of the device of FIG. 13A along plane FF', FIG. 14 is a section view of a variant of the device of FIGS. 12A and 12B comprising interconnections between the MEMS/NEMS, FIG. 15 is a section view of a variant of the device of FIGS. 14A and 14B comprising interconnections between the MEMS/NEMS, FIG. 16 is a section view of another example embodiment of a device according to the invention, in which the assembly between the cap and the substrate is produced by means of a dry film, FIG. 17 is a section view of a variant of the device of FIG. 16 comprising an intermediate layer is formed between the substrate and the cap and within the channel, FIG. 18 is a section view of a variant of the device of FIG. 16 comprising several MEMS/NEMS and an intermediate layer is formed between the substrate and the cap and within the channel, FIGS. 19A to 19H are diagrammatic representations of steps of an example of a method for producing the substrate fitted with at least one MEMS or NEMS structure for the production of a device with fluid channel according to the invention, FIGS. 20A to 20D are diagrammatic views of steps of an example of a method for producing a cap and its assembly with the substrate having the MEMS or NEMS structure(s) for the production of a device with fluid channel according to the invention, FIGS. 21A to 21F are diagrammatic views of steps of an example of a method for producing vias in the assembly of FIG. 20D, FIGS. 22A to 22C are diagrammatic representations of steps of an example of a method for producing a device with fluid channel according to the invention having no intermediate layer, FIGS. 23A to 23F are diagrammatic representations of steps of an example of a method for producing a device with fluid channel according to the invention having no intermediate layer.

DETAILED DESCRIPTION OF PARTICULAR EMBODIMENTS

In the present application the term "NEMS/MEMS portion" is understood to mean a mechanical structure comprising a stationary structure and at least one sensitive structure, and means of actuation and/or transduction of at least one characteristic of the sensitive structure.

Electrical connections are provided to connect the sensitive structure to the external environment. This MEMS/NEMS portion may comprise a network of NEMS and/or MEMS structures, possibly with several metallisation levels to produce the required interconnections. For purposes of simplicity, an MEMS or an NEMS will be designated by NEMS.

The "sensitive portion" can be a suspended portion or a portion which is not suspended. In the remainder of the description these two expressions will be used interchangeably, bearing in mind that in certain applications of the electromechanical type this sensitive portion is mobile.

The term "NEMS structure" is understood to mean, in the present application, a structure comprising one or more NEMS.

The same references will be used to designate the elements having the same functions and approximately the same shape.

In the represented examples the fluid channel is linear along axis X, but a channel having a curved shape, or indeed a spiral or any other shape, does not go beyond the scope of the present invention.

In FIG. 1 a device with fluid channel according to a first embodiment can be seen represented diagrammatically, as a top view, with the top of the cap omitted. In FIG. 2 a cross-section view along plane A-A' of FIG. 1 can be seen. In this view the top of cap 6 is represented.

The device comprises a fluid channel 2 which is linear along axis X in the represented example. Fluid channel 2 is delimited by a substrate 4 and a cap 6 added on to substrate 4 and assembled in an area of an assembly interface 3. For example, the flow in the fluid channel occurs from one longitudinal end 2.1 to the other 2.2 of fluid channel 2.

In the represented example cap 6 is formed from a substrate in which a cavity 5 has been made. Cavity 5 delimits with the substrate bearing the NEMS/MEMS structure and assembly interface 3 fluid channel 2 which causes a gas mixture or liquid blend to flow and be distributed. The channel is delimited by two side walls 6.1, where an upper base 6.2 connects the two side walls 6.1 and a lower base formed by substrate 4. Side walls 6.1 have under-faces which allow the cap to be sealed on to the substrate.

It will be understood that the input end and/or the output end of the fluid channel could, for example, be produced in the upper base 6.2 of the channel or alternatively in substrate 4.

Alternatively, cap 6 could have a more complex shape, for example it could comprise a long channel of optimised shape, for example a spiral, enabling a chromatography column to be produced implementing the function of separation of the compounds of a mixture, where the column comprises one or more NEMS/MEMS structures.

In the represented example cap 6 is assembled on to substrate 4 by sealing.

The substrate comprises a NEMS/MEMS structure 7 located inside fluid channel 2. In the represented example the suspended structure of the NEMS is formed by a beam 10 which is embedded at one of its longitudinal ends; for example two gauges 12, for example two piezoresistive gauges, are used to detect the movement of beam 10. The ends of connection lines 8 connected to the NEMS/MEMS structure can be seen The device also comprises electrical connections 8 extending between the NEMS located in fluid channel 2 and the exterior of the fluid channel. Electrical connections 8 are formed by vias running through substrate 4, also called TSVs (Through Silicon Vias). For purposes of simplicity the vias running through substrate 4 will subsequently be designated "via". The vias run through substrate 4 vertically below the NEMS structure located in the fluid channel and outside the assembly area, more specifically vertically below the stationary portion of the NEMS. In the representation of FIG. 2 the vias are produced under the NEMS.

The vias are preferably produced using a via-last approach, i.e. after production of the NEMS structure(s). The vias then have a diameter of several µm; they are well suited to the mechanical structures and they have relatively high densities since the interval between these vias is of the order of some ten µm. The vias can be made of different materials such as, for example, Cu, W, etc.

As a variant, vias of different natures and geometries can be envisaged. For example, the vias can be wide etched holes covered with a conductive material providing the electrical continuity between the two faces of the substrate. Alternatively, and preferentially, the vias can be formed by relatively narrow holes which are completely filled with a more or less conductive material, for example polysilicon. A narrow hole has, for example, a diameter of approximately several µm and a wide hole has, for example, a diameter of approximately several tens of µm to several tens of µm. As another variant it can be envisaged, for example, to retain the semiconductor material in which the via is formed, and to fill the annular peripheral area which surrounds the semiconductor material with an electrically insulating material to insulate the central portion relative to the remainder of the substrate.

For example, the via(s) can come into contact with the lower face of layer 16 in which the NEMS is/are formed. As a variant, the via(s) can come into contact with the upper face of layer 16, preferentially through a metal contact formed on the surface of layer 16.

As another variant, the via(s) can come into contact on a metal interconnection layer produced in a plane parallel to the plane of the NEMS, on the side of the fluid channel, for example on one of the levels of interconnection of the NEMS networks which will be described below, or on the side of the substrate in which these connection patterns are produced. It could also be envisaged for the vias to come into contact on a metal interconnection layer produced in a plane parallel to the plane of the NEMS, but on the side opposite the fluid channel, to connect to external elements located, for example, to the rear of the MEMS Substrate 4 comprises a stack of a sacrificial layer 14 used to produce the NEMS, a layer 16, for example made of a semiconductor material, in which the stationary portion and the suspended portion of the NEMS are produced.

The vias do not emerge in assembly interface 3, and the assembly interface can then have no metal layer. It is then possible to produce assemblies with sealing techniques which are very efficient in terms of robustness, reliability and hermeticity.

Firstly, the fact that no via emerges in the sealing or connection lines interface between the cap and the substrate enables a flat surface to be provided. Thus, techniques such as molecular sealing, eutectic sealing (AuSn, AuSi, etc.) or metal thermocompression sealing (Au—Au, Al—Ge) can be envisaged. Metal thermocompression sealings are particularly advantageous since they enable the sealing temperature to be reduced below 400° C. or even 200° C., which is particularly advantageous when a functionalisation layer is implemented. Similarly, a molecular sealing, which can be undertaken at low temperature, is advantageous for the same reasons of preservation of a possible functionalisation layer.

If the deposition of a layer is required for the sealing, where this layer can possibly be structured on a single one of the two portions, which is the case for a eutectic sealing, this deposition and this possible structuring are preferably undertaken on the cap. For example, in the case of an Au—Si eutectic sealing, a layer of Au is preferably deposited on the cap.

If deposition of a layer on each of the two portions is required, for example for a thermocompression sealing, deposition on the NEMS/MEMS structure is undertaken before the structure is released. The material of this layer is then chosen such that it is compatible with the method of release of the NEMS/MEMS structure, so that it is not etched in this technological step which occurs just before sealing. A layer of Au will then be used on the cap and on the intermediate layer for an Au—Au sealing, if the NEMS is to be released with vapour phase hydrofluoric acid.

In the case of a molecular sealing or anodic sealing, for example if the cap is made of glass, the sealing interface is formed by the face of the cap and the face of the substrate which is to be sealed. No addition of material is required. The faces intended to come into contact are prepared in a known manner by those skilled in the art, for example by CMP (chemical-mechanical polishing) of layer 16 and of the lower face of cap 6.

A molecular sealing in the presence of a functionalisation layer at the interface, where the functionalisation layer is also deposited after release, is also conceivable.

The vias are advantageously produced after the cap is sealed on to the substrate. In this case high-temperature sealings are conceivable, particularly since there are no active structures of the CMOS type on the substrate.

In addition, the use of vias in the fluid channel enables devices to be produced with a larger number and/or a higher density of electrical outputs of the NEMS structures contained in the fluid channel towards the exterior of this channel. This therefore results in the possibility of having a higher density of NEMS structures (whether or not in networks) inside the fluid channel, which is particularly advantageous in the case of a gas chromatography microcolumn in which NEMS/MEMS structures are distributed throughout the length of the microcolumn.

As a comparison, relative to the lateral connection lines implementing electrical contact contacts of the order of 100 µm×100 µm, this density can be increased by making vias of small diameters, for example several µm or several 10 µm of diameter.

In addition, as was mentioned above, since the vias are produced in the substrate, they are produced independently of the thickness of the "cap" layer. It is then possible to produce dense vias and a deep cavity. This advantage is remarkable in particular in the case of an instrumented microcolumn which requires dense vias, requiring that the NEMS substrate is thinned to some 10 µm, and a dimension of the microcolumn cavities of at least 100 µm. Indeed, the typical dimensions of the channel section are 80×80 µm, or greater, for the requirements of the application to separate the analytes constituting the gas mixture flowing in the channel. The vias are advantageously produced after assembly with the cap, which then allows a sufficient thinning of the substrate, for example of several tens of µm, to produce sufficiently dense vias, with the cap providing the mechanical rigidity.

The invention makes it possible to manufacture the device with complex NEMS networks within the fluid channel, and to have very satisfactory control of these networks, through individual addressing of each NEMS structure through the TSVs.

Furthermore, the materials at the sealing interface such as silicon, metals, oxides, etc., are generally more neutral compared to the species (for example gas), flowing in the fluid channel, compared to a layer of adhesive, which may degas and can have a disruptive chemical affinity relative to the species in circulation. This advantage is particularly useful in the example of a fluid channel intended for the production of a gas chromatography column.

In FIG. 3 the device comprises a functionalisation layer 18 covering layer 16, and the entire NEMS/MEMS structure. This functionalisation layer 18 is said to be non-localised.

The term "functionalisation layer" is understood to mean a layer present at the surface of the mechanical structure, to give it particular properties. For example, in the case of a gas sensor, the functionalisation layer enables the adsorption of gas species, possibly selectively, to be increased or, in the case of a biological sensor, the functionalisation layer allows the grafting of biological species. Functionalisation layer 18 is, for example, formed of one or more organic or inorganic materials, polymers, oxides, carbon compounds, semiconductors or other porous materials.

The invention allows, very advantageously, the step of deposition of the functionalisation layer to be implemented on a previously released mechanical structure, which enables the mechanical structure to be encapsulated almost totally with the functionalisation layer when the deposition of this layer is sufficiently conformal. The functionalisation layer then has a surface which interacts to a greater degree with the surrounding medium, which increases still further the usefulness of a functionalisation layer. The invention allows the implementation of functionalisation layers on NEMS released by collective techniques without liquid contact, for example by CVD, LPCVD, PECVD or ALD, epitaxy, porosification, etc. and this to be followed by closing the component by adding a cap with a cavity so as to form the fluid channel. By this means the risks of adhesion by deposition of the functionalisation layer by deposition in the liquid phase are prevented.

In FIG. 4 functionalisation layer 118 is present only on the sensitive portion of the NEMS, and the functionalisation layer is said to be localised.

The invention allows, very advantageously, the step of deposition of the functionalisation layer to be implemented on a previously released mechanical structure, which enables the mechanical structure to be encapsulated almost totally with the functionalisation layer when the deposition of this layer is sufficiently conformal. The functionalisation layer covers the upper face, the lower face and the side faces of the suspended element. The functionalisation layer then has a surface which interacts to a greater degree with the surrounding medium, which increases still further the usefulness of a functionalisation layer. The invention allows the implementation of functionalisation layers on NEMS released by collective techniques without contact, for example by CVD, LPCVD, PECVD or ALD, epitaxy, porosification, etc. and this to be followed by closing the component by adding a cap with a cavity so as to form the fluid channel. By this means the risks of adhesion by deposition of the functionalisation layer by deposition in the liquid phase are prevented.

In FIGS. 5A and 5B a device according to a particularly advantageous embodiment of the invention can be seen implementing an additional layer 20 called an "intermediate layer".

According to a first example represented in FIGS. 5A and 5B, intermediate layer 20 is positioned at the assembly interface only. It is interposed between layer 16 made of a semiconductor material and cap 6. The presence of intermediate layer 20 at the assembly interface facilitates assembly. Indeed, the intermediate layer can have a surface condition allowing sealing with the faces of the base of the cap, for example a dry film sealing, a molecular, eutectic or thermocompression sealing. The face fit for sealing can have a certain roughness or a certain relief which nevertheless allows sealing.

Intermediate layer 20 is present at least at the sealing interface between NEMS/MEMS structure 7 and the cap and is absent from the sensitive areas of the NEMS/MEMS structure, in order to leave the portion or portions of the suspended NEMS/MEMS structure in contact with the medium present in the fluid channel.

The material of intermediate layer 20 is chosen such that it is possible to obtain a face 20.2 which is sufficiently flat for sealing the cap. Depending on the type of sealing, the surface condition of face 20.2 obtained directly after the deposition of the intermediate layer can be sufficient, or a step of planarisation is accomplished, for example a step of chemical-mechanical polishing after the formation of the intermediate layer.

The material of the intermediate layer is chosen such that it can be etched, for example by anisotropic etching.

The material of intermediate layer 20 is preferably chosen such that it has a satisfactory etching selectivity compared to the method of release of the mechanical structures, and does not generate any residue in this step.

The material of the intermediate layer is also chosen such that it is compatible with the materials used for the final assembly of the device between the substrate bearing the NEMS/MEMS structure and the cap.

If a functionalisation layer is implemented, the material of the intermediate layer is chosen such that it is compatible with that of the functionalisation layer, in particular so as to provide satisfactory adherence of the latter.

For example, the material of the intermediate layer is a dielectric material, for example a silicon oxide, such as for example $SiO_2$ or an oxide formed from silane or an oxide formed from tetraethyl orthosilicate (TEOS), a silicon oxide of the LTO (Low Temperature Oxide) type formed by LPCVD (Low Pressure Chemical Vapour Deposition), which is either undoped or alternatively doped with phosphorus (PSG: Phospho-Silicate-Glass) or again doped with boron and phosphorus (BPSG: Boro-Phospho-Silicate Glass), an oxide deposited by PECVD (Plasma Enhanced Chemical Vapour Deposition).

The thickness of the intermediate layer is determined taking account of the consumption of the material during the release etching. In this case the thickness of the intermediate layer is, for example, of the order of several μm.

As a variant the intermediate layer can comprise two layers. A layer of dielectric material forming the planarising layer is deposited. The planarising layer is, for example, an oxide formed from silane $SiH_4$, or alternatively an oxide formed from tetraethyl orthosilicate (TEOS). A protective layer, made for example of amorphous Si, silicon nitride, metal (AlSi, AlCu, etc.) or hafnium oxide (HfO2), is then deposited on the planarising layer, and the latter increases the resistance to etching using hydrofluoric acid vapour.

In FIG. 6A a variant embodiment can be seen in which a non-localised functionalisation layer 18 is produced; it is then located on face 20.2 of the intermediate layer.

In FIG. 7 a variant embodiment can be seen in which a non-localised functionalisation layer 118 is produced; it is located only on the sensitive portion of the NEMS.

In FIGS. 8A, 8B and 8C, another example embodiment of a device implementing an intermediate layer can be seen. In this example intermediate layer 120 is located at the sealing interface and inside the fluid channel.

In FIG. 8A the intermediate layer delimits a channel 21 within the channel with a width such that it leaves the sensitive portions of the NEMS structure free.

In FIG. 8B the intermediate layer leaves free only the sensitive portions of the NEMS structure, and the intermediate layer is present upstream and downstream of the NEMS structure.

In this example embodiment, in addition to its presence at the sealing interface, the intermediate layer encapsulates the materials used in the NEMS, leaving accessible for the fluid circulating in the fluid channel only the sensitive portion of the NEMS or of a network of NEMS.

This encapsulation has the advantage that it isolates the materials used in the NEMS portion which, through their presence in fluid channel 2, could interact with the medium circulating in the channel. This is the case, for example, with the metals or dielectrics which are generally used in the fluid channel if the mechanical structure is formed of a dense network of NEMS.

A device with fluid channel in which the intermediate layer does not entirely cover the portion of the NEMS/MEMS structure not intended to come into contact with the surrounding medium does not go beyond the scope of the present invention.

By this means the interactions between the materials used in the NEMS and the medium present in the fluid channel are prevented.

In addition, the intermediate layer forms a quasi-flat surface in the area surrounding the sensitive portions of the NEMS, forming a fourth face of the fluid channel.

As can be seen in particular in FIG. 8C, intermediate layer 120 is present above layer 16 in which the NEMS is produced, which is made for example of a semiconductor material, in the area of the vias which are, for example, made of metal. The presence of the intermediate layer mechanically strengthens the structure, in particular with regard to the mechanical stresses which can be caused in the vias, for example due to differences of thermal expansion coefficient between the material of the vias and the surrounding material in which these vias are formed. The reliability of the device is then improved.

In FIG. 9 a variant embodiment can be seen in which a non-localised functionalisation layer 18 is produced; it is then located on face 120.2 of the intermediate layer.

In FIG. 10 a variant embodiment can be seen in which a non-localised functionalisation layer 118 is produced; it is located only on the sensitive portion of the NEMS.

In FIGS. 11A and 11B another example embodiment of a device implementing an additional layer, called the "encapsulation layer", 220 can be seen, which is present only inside the fluid channel, and covers the materials used in the NEMS.

Encapsulation layer 220 has the same advantages as layer 120, except for those relating to the sealing.

In a manner similar to the variants of FIGS. 9 and 10, the device of FIGS. 11A and 11B can comprise a functionalisation layer either localised on the sensitive portions of the NEMS structure, or not localised; it would then be located at the assembly interface, on encapsulation layer 220 and the sensitive portions of the NEMS structure.

In FIGS. 11A and 11B an example embodiment of a device implementing multiple NEMS in the fluid channel can be seen. The NEMS may or may not be interconnected. An example of a device with interconnected NEMS will be described below.

In the represented example three pairs of NEMS are aligned along axis X.

In FIGS. 12A and 12B an example embodiment of a device with several NEMS structures 7 can be seen, where each of these structures can be connected to a via. It should be noted that in FIGS. 12A and 12B there are no metal interconnections on the side of the fluid channel, nor any represented intermediate layer. However, such an intermediate layer can be implemented in the different configurations described above.

For example, in FIGS. 13A and 13B an intermediate layer 120 is formed between the cap and the substrate and in the channel, leaving free only the sensitive portions of the NEMS structures.

In FIG. 14 a device comprising a network of interconnected NEMS can be seen. In this example the interconnections between NEMS are made by conductive connections, preferably metal connections, 24, formed on the NEMS in the fluid channel.

Interconnection lines 24 are then made on several levels of metal, two such in the represented example, in order to interconnect the NEMS forming the network of NEMS, which is located inside the fluid channel. Interconnections with one or more than two metal levels do not go beyond the scope of the present invention.

This configuration enables the flatness of the surfaces surrounding the NEMS to be preserved, and in particular the assembly interface, by this means facilitating assembly of the cap and of the substrate. The via(s) can come into contact on one of the connection lines, as described above.

As a variant, the NEMS can be interconnected electrically, either directly through connection patterns 8 and/or through interconnection patterns in addition to the device of the invention, or by means comprised in the device, for example by an electrical routing layer formed on rear face I, or by means external to the device, for example by an electronic card or an integrated circuit connected to the device by flip-chip or copper pillar techniques, or other techniques well known to those skilled in the art in the 3D integration field.

As another variant, the NEMS can be interconnected through interconnection lines made in the material of layer 16 and/or through one or more metal layers produced in the planes parallel to layer 16. In the latter case the metal interconnections can be electrically insulated from one another by air, or indeed one or more dielectric materials.

In FIG. 15 a variant of the device of FIG. 14 can be seen in which an intermediate layer 120 is implemented. Very advantageously the electrical connections are encapsulated by intermediate layer 120 in an electrically insulating material, for example made of silicon oxide leaving only the sensitive portions accessible. This encapsulation enables the materials of the interconnections to be insulated from the fluid flowing in the channel, and by this means enables undesired reactions with it to be prevented. This intermediate layer also forms a fourth face of the fluid channel.

The different metallisation levels are partially encapsulated in electrically insulating layer 120 made, for example, of silicon oxide.

This encapsulation by the intermediate layer is particularly advantageous to implement in the case of NEMS which are interconnected by conductive tracks made of semiconductor material or of metal, possibly with several levels of interconnections, where the electrical insulation between the levels is provided by layers of dielectrics, and the whole assembly is localised in the fluid channel.

In FIGS. 16 to 18 devices can be seen represented in which the assembly is accomplished by means of a Dry Film Resist or DFR 22.

For example, a thin resin film is applied by lamination on to the lower face of cap 6 intended to come into contact with layer 16 (FIG. 16) or intermediate layer 20 (FIGS. 17 and 18) and is structured by photolithography and development. The cap and resin film assembly is transferred and sealed on the substrate.

In the example represented in FIGS. 16 to 18 thin film 22 takes the form of two parallel beads, having roughly the same sealing area. These beads are obtained after insolation and development of the dry film.

The dry film is, for example, a resin with epoxy, phenol, acrylic or silicone bases, for example.

The dry film is, for example, between several µm and several tens of µm thick, or several hundreds of µm thick with a multi-layer of dry film, and advantageously only several µm thick.

Sealing by means of a dry film has the following advantages:

- this type of sealing can take place at a relatively low temperature, generally below 250° C., or at ambient temperature, which is compatible with the existence of metal tracks. Indeed, in the case of aluminium tracks the maximum temperature is 400° C.

this type of sealing is compatible with a large number of materials, the dry film can be produced on the cap despite the strong topology due to the previously formed fluid channel, which enables no operations of the photolithography type to be undertaken on the NEMS/MEMS structure, since the latter already contains released mechanical structures, this type of sealing by dry film has the advantage that it is less demanding in terms of the required surface condition (flatness, roughness, presence of particles) at the sealing interface than sealings of the molecular or eutectic type, or even thermocompression sealings. Thus the use of a dry film can allow sealing without undertaking any prior chemical-mechanical polishing of the face of the substrate on which the sealing is accomplished, for example face 20.2 of the intermediate layer (FIGS. 17 and 18), and its surface condition directly after deposition can be sufficient.

This characteristic advantageously enables this sealing to be accomplished in the presence of a functionalisation layer at the assembly interface. In addition, the temperature of such sealing is compatible with the presence of a functionalisation layer which is deposited or itself formed at low temperature, for example made of polymer, etc.

This type of film also provides the possibility of working with large thicknesses, for example of the order of several hundreds of μm, but also thicknesses of several 10 μm; or several μm, since a small thickness enables the thickness of the material of the dry film able to interact with the surrounding medium to be limited.

This type of film also has satisfactory thermal stability.

In addition, since this type of sealing is compatible with a large number of materials, great freedom is available in the choice of functionalisation layer or layers which can be implemented. It is then possible to envisage implementing functionalisation layers of different natures and/or thicknesses on the NEMS and cap portions. This is particularly advantageous if the cap forms a gas chromatography column. In this case the cap will be able to receive a functionalisation which is able to fulfil the function of separation of the analytes of the mixture or blend to be analysed, while the NEMS will be able to receive another functionalisation able to optimise its detection efficiency.

If a functionalisation layer is implemented the sealing is advantageously accomplished by the dry film technique.

We shall now describe examples of methods of producing devices with fluid channel according to the present invention.

The method which will be described allows the production of several NEMS simultaneously in a fluid channel aligned along the longitudinal axis, where a single one is visible. It will be understood that the method allows the production of several devices simultaneously with one or more NEMS, where the devices are then separated at the end of the manufacturing method.

In a first phase the substrate comprises the NEMS/MEMS structure is produced from an SOI (Silicon On Insulator) substrate, for example. Alternatively, any substrate comprising a layer in which the NEMS/MEMS is produced can be used, where this layer is formed on a sacrificial layer allowing release of the NEMS/MEMS structure through etching of it. The material of the layer in which the NEMS/MEMS structure is produced can be a monocrystalline or polycrystalline semiconductor material, for example Si, Ge, SiGe, SiC, GAAs, InAs, InP, etc. The sacrificial layer can be present over the whole substrate, or alternatively be localised only at certain places where the NEMS will be produced.

It can be envisaged that the NEMS/MEMS structure comprises an optical function so as to comprise MOEMS (Micro-Opto-Electro-Mechanical Systems) and/or comprise an integrated electronic portion, CMOS, etc.

The first example of a method which will be described enables a device according to the invention to be produced comprising an intermediate layer and a localised functionalisation layer with a level of interconnections in the area of the NEMS as represented for example in FIG. 7.

The SOI substrate comprises a layer of insulating material 28, for example made of silicon oxide, and a silicon layer 30 in which the NEMS structure will be formed.

In a first step the silicon layer 30 is doped. To accomplish this a protective oxide layer is formed on doped layer 30, for example a thermal oxide, followed by a step of implantation, followed by annealing and deoxidation by removal of the oxide layer.

The doping can be accomplished in a full-plate manner or using masking, for example using a resin if it is desired to localise areas with different types of doping. For example it is possible to envisage a medium to moderate (several $10^{18}$ to several $10^{19}$ at/cm$^3$) P-type doping (boron, for example) or N-type doping (phosphorus, for example) in the NEMS area, depending, for example, on whether it is desired to optimise the piezoresistive gauge factor and/or the noises, and a strong doping (several $10^{20}$ at/cm$^3$) in the area of the contact contacts intended to receive the metal of the vias on their lower face, so as to provide a satisfactory ohmic contact.

Figure 19A:
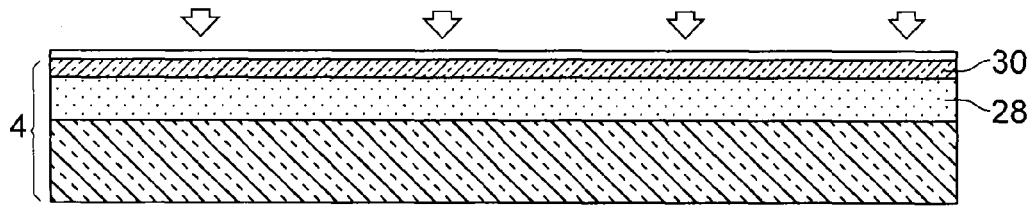

The element obtained in this manner is represented in FIG. 19A.

In a subsequent step the NEMS structures and the electrical contact contacts are defined.

To do so a photolithograph and then an anisotropic etching of silicon layer 30 are accomplished in a known manner.

A step of stripping then takes place on the silicon and on oxide layer 28 to remove the layer of photosensitive resin.

Figure 19B:
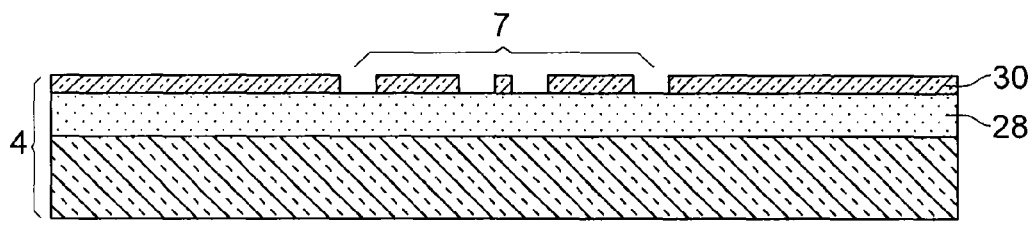

The element obtained in this manner is represented in FIG. 19B. In FIG. 19B, which is a section view, a single NEMS can be seen, but the structure preferably comprises multiple NEMS in direction X. The structure could also comprise several NEMS in a direction perpendicular to direction X.

In the next steps the metal interconnection lines are made. To do so a deposition of a dielectric layer 32 on structured layer 30 then takes place; this is, for example, an oxide formed from silane SiH$_4$ the thickness of which is greater than the topology of structured silicon layer 30.

A step of chemical-mechanical polishing or CMP then takes place to make the surface of layer 32 flat. Prior to this a photolithograph of the "counter mask" type and a partial etching of layer 32 of the height of the topology to be made up are preferably undertaken, which facilitates the step of polishing, and enables its duration to be reduced.

In a subsequent step layer 32 is opened by photolithography and etching to reach silicon layer 30, and to prepare for the production of the electrical contact contacts and/or the interconnection lines between NEMS.

Figure 19C:
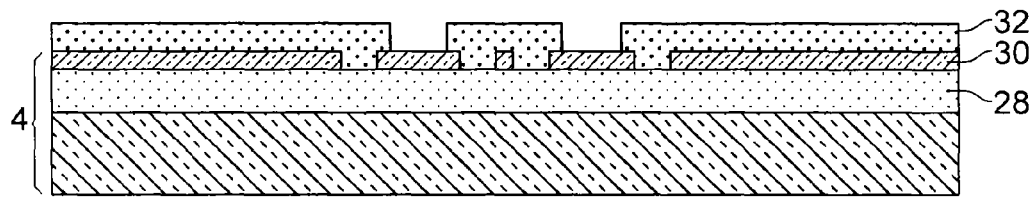

The element obtained in this manner is represented in FIG. 19C.

In a subsequent step, a metal layer 34 is deposited, made for example of AlSi, since the latter has the advantage that it provides satisfactory resistance to the etching by hydrofluoric acid vapour, which takes place to release the mechanical structures. The thicknesses of formed layers are chosen so as to facilitate subsequent planarisation.

In a subsequent step chemical-mechanical polishing takes place.

Figure 19D:
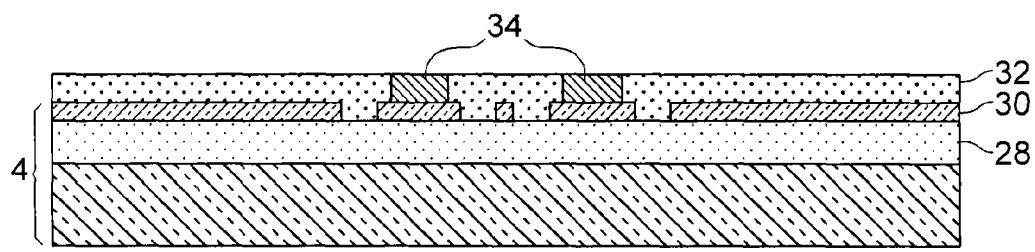

The element obtained in this manner is represented in FIG. 19D.

In the represented example layer 32 is preserved. As a variant it can be removed, and advantageously etched selectively relative to the metal of the interconnection lines, in order to preserve the interconnection and/or metallisation lines of the contact contacts. It can be fully removed or removed only partially, for example in the areas intended for the assembly. The steps of production of the contact contacts and/or of the interconnection lines can be repeated several times in order to produce several levels of metal interconnections. These steps can also enable electrical interconnection lines to be produced between different NEMS on one or more levels. The interconnection lines are then insulated from one another by the material of layers 32.

The subsequent steps describe the production of intermediate layer 20.

In the represented example intermediate layer 20 has two layers. A layer of dielectric material 35 is deposited, for example a silicon oxide formed from silane $SiH_4$, or alternatively a silicon oxide formed from tetraethyl orthosilicate (TEOS). A protective layer 36, made for example of amorphous Si, silicon nitride, metal (AlSi, AlCu, etc.) or hafnium oxide (HfO2), is then deposited on the planarising layer, and the latter increases the resistance to etching using hydrofluoric acid vapour used to release the NEMS.

In the case of an intermediate layer made of a single material its thickness is determined such that it is able to protect, in particular, the connection lines in the final step of release of the mechanical structures, i.e. its thickness is chosen such that it is sufficient to take account of the reduction due to the release etching, in order that it still covers the connection lines. As mentioned above, the thickness of the intermediate layer in this case can be, for example, of the order of several μm.

In this example intermediate layer 20 is formed on metal interconnection lines and/or electrical contact contacts, but it could be implemented directly on the NEMS layer (with or without metal interconnection lines or electrical contact contacts), etc. It should be noted that layer 32 could have been removed after formation of the interconnection lines; intermediate layer 20 would then have been formed directly on these lines.

Figure 19E:
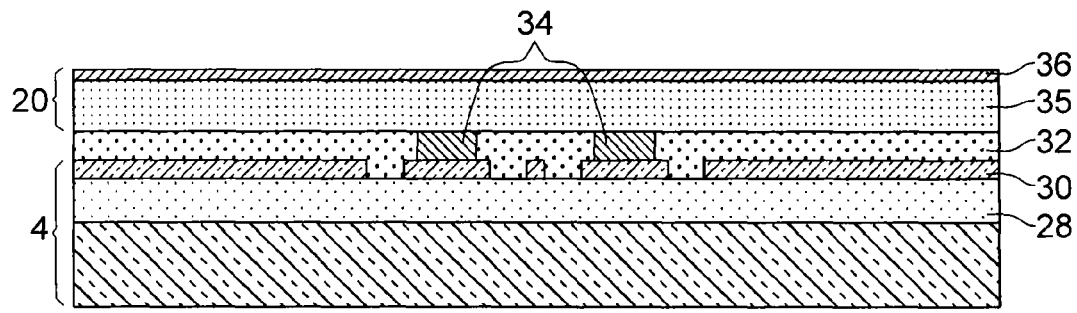

The element obtained in this manner is represented in FIG. 19E.

A step of polishing, for example by CMP, of layer 32 prior to the deposition of layer 20 can take place.

In a subsequent step the intermediate layer is etched so as to reach the NEMS/MEMS structure to be released. Layer of amorphous Si 36 and layer 35 are etched, and layer 32 can also be partially or totally etched. For example, it is possible to use an $SF_6$ plasma etching for the layer of amorphous Si and a $CHF_3$ plasma etching for the etching of the silicon oxide forming the intermediate layer.

Intermediate layer 20 can be etched in different ways to produce the different devices described above. It is thus possible to etch it only above the sensitive portions by protecting the remainder of the surface, in order that the intermediate layer is at the assembly interface and in the fluid channel, or then only at the assembly interface or, alternatively, only in the fluid channel, in which case it has solely an encapsulation function.

Etching of intermediate layer 20 is chosen so as to preserve both the metal interconnections and the NEMS/MEMS structure made of a semiconductor material. In this manner the shape of the apertures is determined for example by photolithography so as to take account of the length of release of the mechanical structures which occurs at the end of the "NEMS" method, since this step can cause an undesired lateral etching of the planarising layer of intermediate layer 20 which, if it were not controlled, could lead to the release of undesired areas such as metal interconnections, areas under the sealing interface with the cap. In addition, etching of the aperture in the intermediate layer is preferably stopped in the metal layer above the semiconductor, before reaching the semiconductor, in order that the semiconductor layer constituting the mechanical structure is not damaged.

Figure 19F:
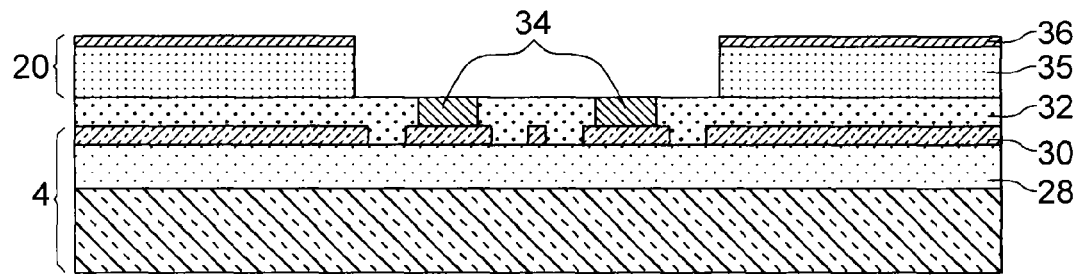

The element obtained in this manner is represented in FIG. 19F.

In a subsequent step the NEMS/MEMS structure, in particular mobile portion(s) 10, is/are released. Release takes place, for example, by isotropic etching using hydrofluoric acid vapour of the dielectric materials surrounding the NEMS structure; these are layers 28 and 32. Layer 28 can be totally or partially etched. Due to the presence of protective layer 36 layer 35 is protected and its thickness is not reduced.

Figure 19G:
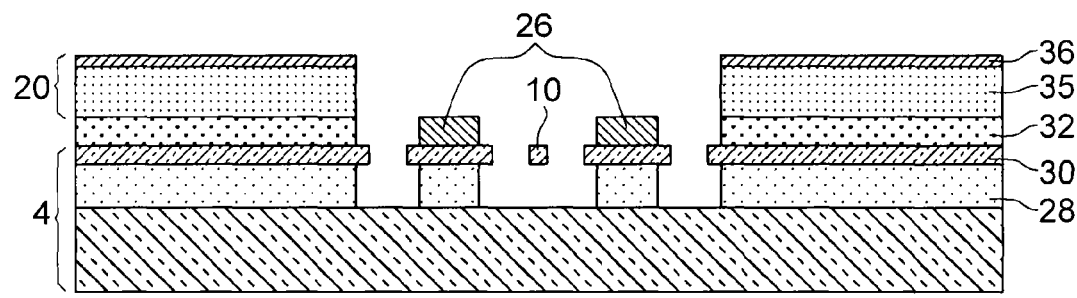

The element obtained in this manner is represented in FIG. 19G.

Figure 19H:
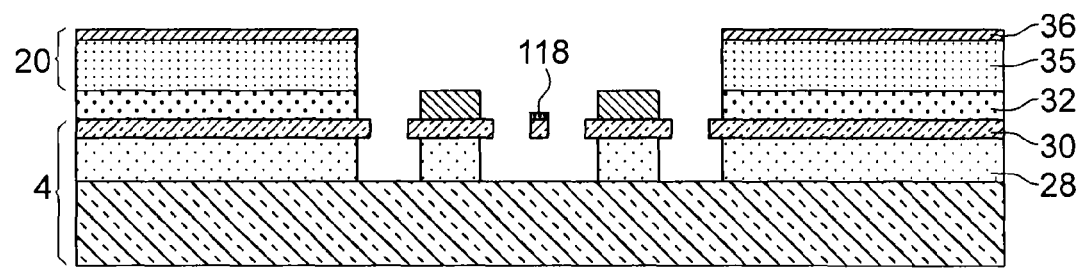

In FIG. 19H the element of FIG. 19G is represented comprising a functionalisation layer 118 which is localised on suspended portion 10 of the NEMS. As a variant, this layer could be non-localised. As a variant it is also possible not to have any functionalisation layers.

This functionalisation layer can be produced in different ways by liquid or gaseous phase depositions. Techniques of gas phase deposition, for example by CVD (Chemical Vapour Deposition), by LPCVD, by PECVD, or by ALD (Atomic Layer Deposition), etc. are preferentially used. Techniques of epitaxy and/or of porosification of materials and/or of the evaporation type can also be implemented. These techniques are preferable to the liquid techniques, of the spraying or spotting type, since they enable the use of liquid phases in the presence of released NEMS structures to be avoided. However, these latter techniques can also be used, for example if the NEMS/MEMS structures are sufficiently rigid.

The deposited materials forming the functionalisation layer(s) can, for example, be materials of the polymer type, dielectrics, semiconductor materials or other porous materials, metals, etc.

In the case of a localised deposition, mechanical masking (stencil) techniques can be used, or lift-off techniques known in methods for producing microsystems, or again spotting techniques, consisting in depositing drops of liquid solution locally, etc.

In FIG. 19H the functionalisation layer is represented only at the surface of the NEMS. The functionalisation layer preferentially surrounds the NEMS, and the thickness of the functionalisation layer is not necessarily uniform all the way round the mechanical structure. This deposition is obtained by using conformal deposition techniques, for example by CVD.

An example of steps of production of cap 6 will now be described on the basis of a substrate 38 which is polished on both faces, for example made of silicon, glass, quartz, etc., designated cap substrate 38.

Firstly, marks (not represented) are defined and then etched in rear face 38.1 and in front face 38.2 of the substrate, these marks being used for alignment between the NEMS substrate and the cap when they are sealed.

Figure 20A:
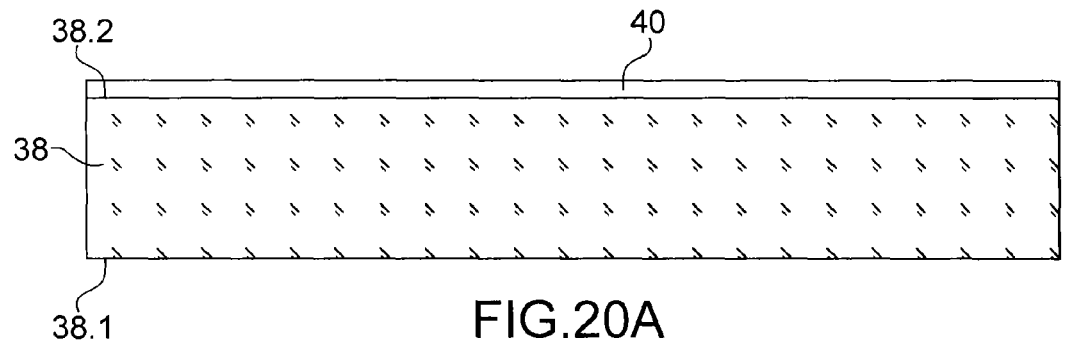

In a subsequent step a deposition of a hard mask, for example a silicon oxide mask several μm thick, is made on front face 38.2 of substrate 38 (FIG. 20A). A photolithograph and etching of mask 40 take place to define the cavities.

Cap substrate 38 is then etched, for example by DRIE (Deep Reactive Ionic Etching) with, for example, a method of the "Bosch" type, consisting in a succession of etching steps with a $SF_6$ plasma and of passivation with a $C_4F_8$ plasma, by this means forming the cavities which will delimit the fluid channels. The depth of the etching is, for example, of the order of several hundred μm.

The hard mask can then be removed, for example by wet etching of the HF type.

Figure 20B:
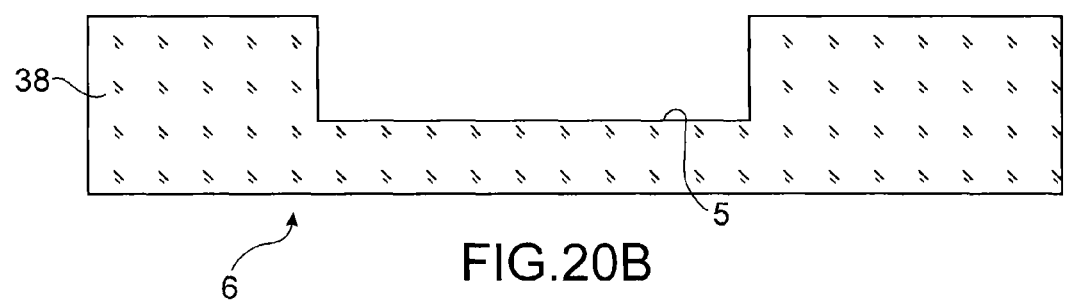

The element obtained in this manner is represented in FIG. 20B.

Two steps of lithography can then be accomplished if it is desired to obtain several etching depths, for example a first depth for the fluid channel and a second depth to produce the inlet(s) or outlet(s) of the fluid channel.

As with the NEMS, the fluid channel can be functionalised by depositing materials on the inner faces of the etching made in the cap; the materials can be those of the functionalisation layer of the NEMS structure, or other materials.

We shall now describe a preferential example of assembly of the cap on the substrate, by a dry resin film. In a preferred manner, and as will be described, the dry film is formed on the cap.

In a subsequent step, cap 6 is prepared for sealing on the NEMS/MEMS structure by means of a dry film. The cap's sealing surface is prepared so as to provide satisfactory adherence of the dry film on the cap.

Dry film 22 is then attached to front face 38.2 of cap substrate 38, this attachment advantageously being obtained by lamination. This lamination enables the technique to be used despite the strong topology due to the existence of the fluid channels on this side of the substrate.

Figure 20C:
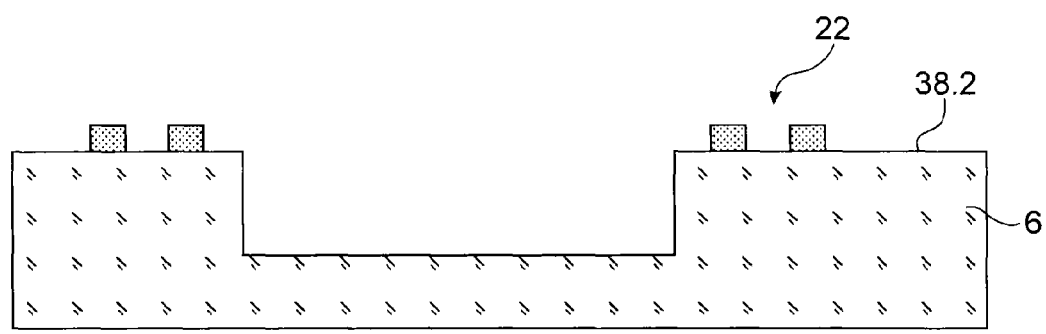

In a subsequent step lithography and development are accomplished to structure the dry film, and the latter then has beads along the cavities etched in the cap. This may be a broad bead, or alternatively, and preferably, several narrow beads which are parallel to one another, as is represented in FIG. 20C. In this latter case, for example, the beads and the spaces between the beads can measure between several μm and several tens of micrometers.

The beads preferably have a regular structure and a close sealing surface over the entire structure to be sealed, to ensure uniform crushing of the dry film with a reasonable pressure in the sealing step.

The element obtained in this manner is represented in FIG. 20C, and cap substrate 38 is then ready to be sealed on to the substrate of NEMS/MEMS structure 4.

As a variant, as was described above, other sealing techniques can be used to assemble the cap and the substrate. In this case other preparatory steps can be implemented, for example special cleaning steps. Sealing techniques known to those skilled in the art can subsequently be implemented, such as for example molecular sealing or again eutectic sealing techniques, or metal sealing techniques, for example by thermocompression, where some of these sealing techniques can require the prior formation of metal beads.

In a subsequent step, cap 6 and substrate 4 comprising the NEMS/MEMS structure are sealed. Sealing is accomplished using sealing equipment which enables the temperature and pressure applied between the cap and the substrate to be sealed to be controlled. Surface treatments known at the state of the art may possibly be undertaken to optimise the adhesion energy.

Substrate 4 and cap 6 are firstly aligned by means of the marks made previously on the substrates.

Pressure is then applied between substrate 4 and cap 6, and a certain temperature is also applied.

The applied pressure is, for example, of the order of several kN to several tens of kN, and the temperature is, for example, between 100° C. and 200° C.

Substrate 4 and cap 6 are then assembled. The fluid channel is then fluid-tight at the lateral edges. The element obtained in this manner is represented in FIG. 20D.

Figure 20D:
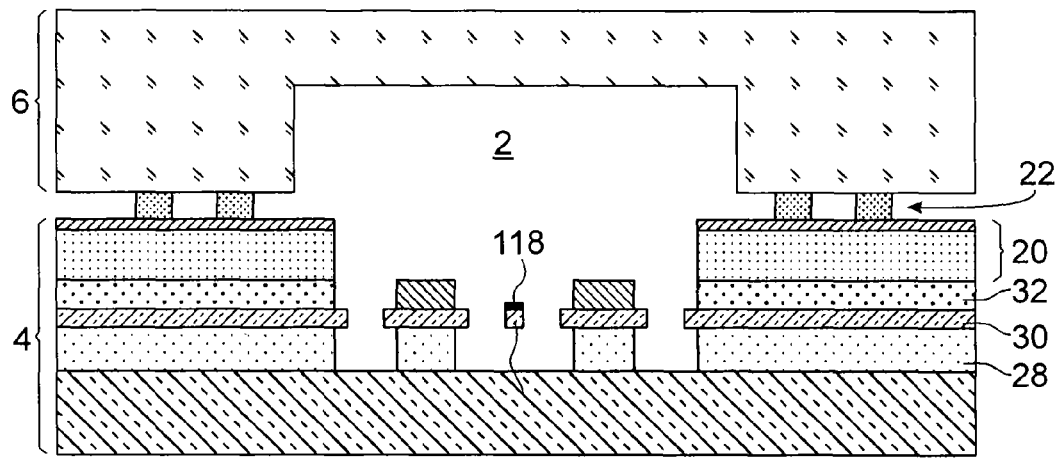

An assembly such as the one of FIG. 20D is typically produced from circular substrates used in the microelectronics field.

The steps of production of the vias will now be described.

Preferably, in a step the silicon substrate in the rear face is thinned, for example by grinding and subsequently by chemical-mechanical polishing. By thinning the substrate in the rear face the depth of the vias is advantageously limited and the operations to fill the cavities with the metal are facilitated.

The remaining thickness of the substrate is such that sufficient thickness is retained to preserve a non-embrittled assembly. The substrate in the rear face advantageously has a remaining thickness of the order of 15 μm to 50 μm, for vias of several μm wide, for example 5 μm. This width enables a high contact density to be provided. With form factors of the order of 2 to 10 the via depths are then approximately 10 to 50 μm. These dimensions at once allow a high via density and preserve a thickness of the layer of the substrate remaining after thinning which is sufficient for the area of the substrate forming the lower base of the fluid channel to resist the thinning operations.

The depth of the fluid channel can, for example, measure several tens of μm to several hundreds of μm, typically 100 μm for a 100 μm width.

Very advantageously, the thinning step takes place after the step of sealing of the cap and of the NEMS substrate, such that the cap acts as a "handle" in the operations to thin the NEMS substrate. By this means it is possible to obtain sufficient thinning of the substrate to attain the desired via densities whilst retaining sufficient mechanical properties.

As a variant, the thinning step can be accomplished by chemical etching, plasma etching, etc.

Figure 21A:
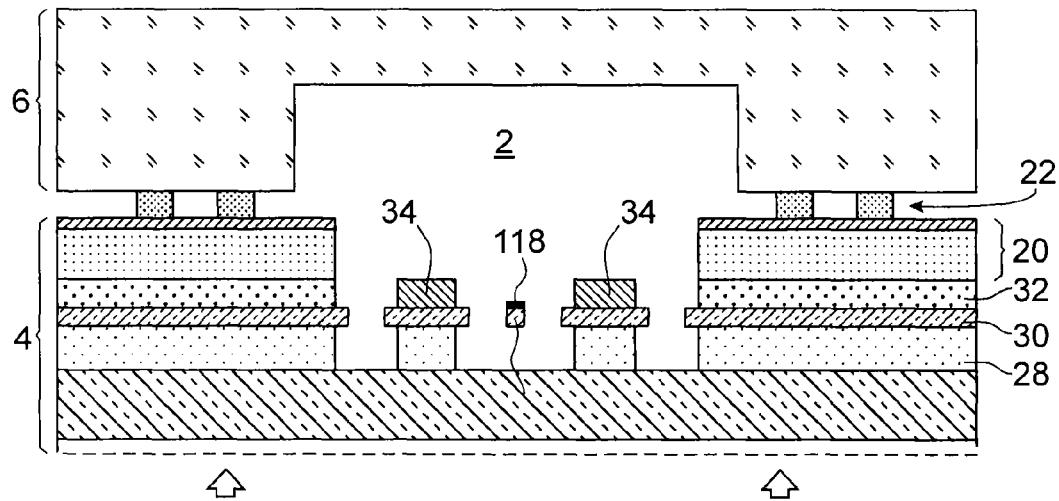

The element obtained in this manner is represented in FIG. 21A.

Figure 21B:
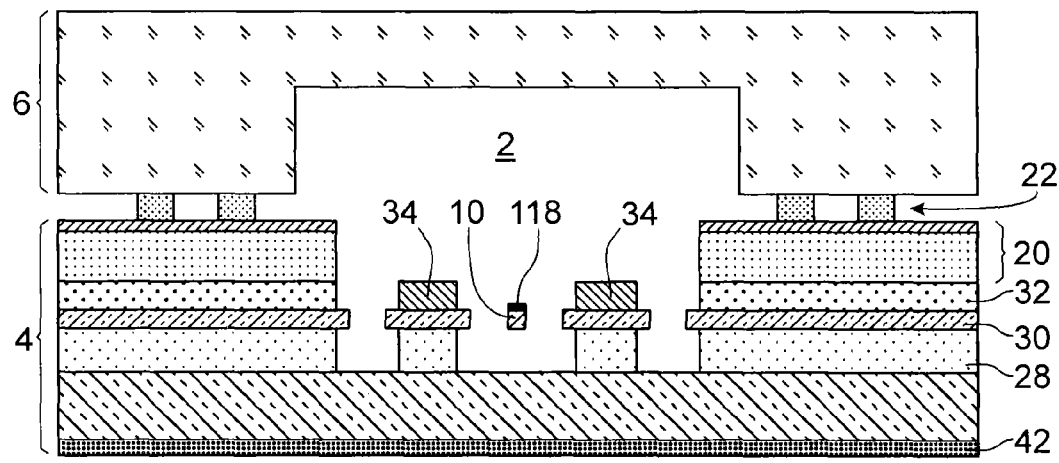

In a subsequent step a layer of dielectric material 42 is formed in the rear face, which is for example several μm thick. layer 42 is, for example, silicon oxide deposited by PECVD, for example. The purpose of this layer 42 is to isolate the vias from a redistribution portion, also called the RDL (Redistribution Layer), which will be combined in a subsequent step, in order to connect the device with vias to an external electronic circuit. The element obtained in this manner is represented in FIG. 21B.

In a subsequent step the vias are produced in the thinned substrate.

To accomplish this layer 42 is structured, for example by lithography and anisotropic etching, for example by $CHF_3$ plasma. Silicon substrate 27 is then etched, for example by $SF_6$ plasma DRIE and $C_4F_8$ passivation, and sacrificial layer 28 is also etched, for example by $CHF_3$ plasma, with the etching stopped at NEMS layer 30. The holes formed in this manner are designated 44.

In a preferred manner a first deep etching is undertaken stopping at oxide layer 28, and a fine etching is then undertaken to reach layer 30 and prevent it being damaged.

Figure 21C:
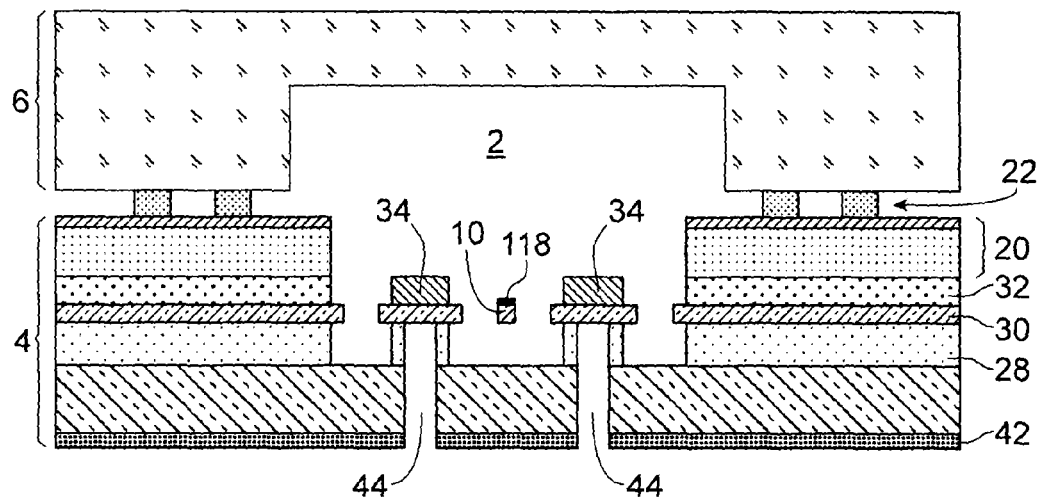
Figure 21C:
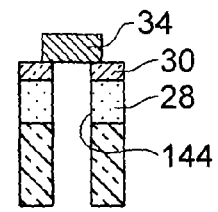

The element obtained in this manner is represented in FIG. 21C.

As a variant, the etching stops at the contact contacts and/or the interconnection lines (FIG. 21C') in order to produce a metal/metal contact between the via and the contact or the interconnection line instead of a metal/silicon contact; layer 30 will then also be etched when the via is etched.

The resin is then removed.

The etching methods are chosen advantageously in order to prevent sub-etching and scalloping effects along the walls.

The dimensions of the holes are, for example, of the order of 2 μm to 10 μm wide and 10 μm to 100 μm deep. These dimensions allow steps of etching, cleaning of the via bases, conformity of the filling materials, etc.

As a variant, the etching could be accomplished by laser drilling, but stopping at layer 30 can be more complex.

In a subsequent step a layer of electrically insulating material 46 is formed on the inner face of holes 44, for example by deposition, where the material advantageously has very satisfactory conformity, for example it is an $SiO_2$ dielectric formed by SACVD (Sub-atmospheric Chemical Vapour Deposition) measuring several hundreds of nm, to produce the lateral electrical insulation of holes 44.

Other electrically insulating materials can be used, for example other types of $SiO_2$ and other dielectrics, for example a polymer.

Figure 21D:
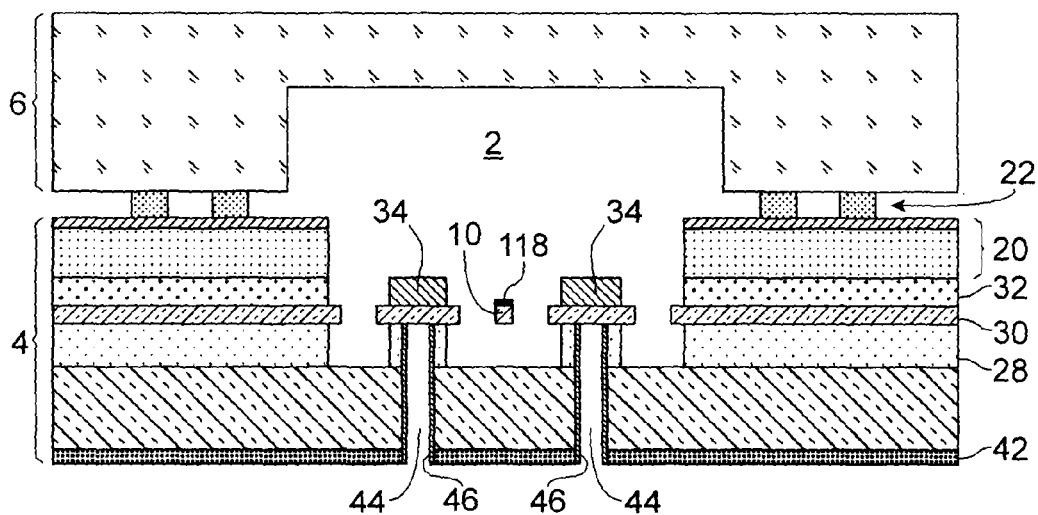
Figure 21D:
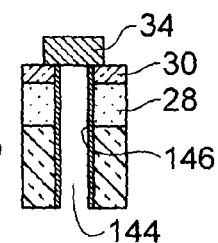

The element obtained in this manner is represented in FIG. 21D.

In FIG. 21D' holes 144 are covered with a layer of electrically insulating material 146.

As a variant, the etching described in relation with FIG. 21B stops in sacrificial layer 28, which reduces the risks of damage of the NEMS layer, which is fine with regard to the thickness etched in the substrate. The electrically insulating layer is then deposited and the etching is resumed to reach NEMS layer 30.

A step of cleaning and of surface preparation at the via base then takes place.

A barrier layer (not represented) is then formed at the base of the hole and on the side walls of the holes, for example made of TiN, Ti, Ta, TaN, etc., for example measuring several tens of 10 nm. This is, for example, deposited by sputtering or CVD, etc.

In a subsequent step a seed layer is formed, for example made of copper by PVD and/or CDV and/or sputtering to prepare for the filling of the via by a metal. This layer is, for example, between several tens of nm and several hundreds of nm thick.

In a subsequent step the holes are filled with an electrically conductive material 48 so as to form vias. The electrically conductive material is preferably metallic, for example made of Cu, W, or strongly doped polysilicon Si, for example.

Filling is accomplished, for example, by ECD (Electro Chemical Deposition). Thermal annealing can then take place. Filling can also be accomplished by CVD or PVD, where these techniques enable satisfactory conformity of the filling to be ensured.

A step of chemical-mechanical polishing then takes place to planarise the assembly and to remove the surplus Cu.

Figure 21E:
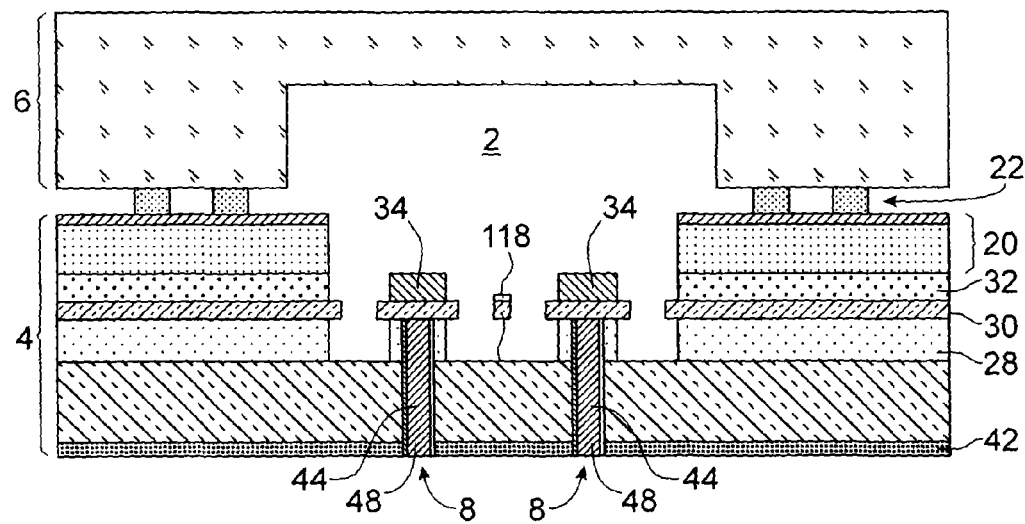
Figure 21E:
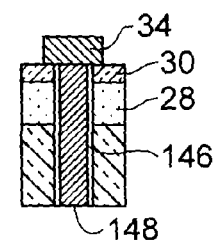

The element obtained in this manner is represented in FIG. 21E; the electrically conductive material of the via is in contact with the silicon of the NEMS; for example it is the Cu/Si or W/Si contact. In FIG. 21E' conductive material 148 is in contact with the metal present at the surface of the contact contact or of the interconnection line, for example it is the Cu/Cu or Cu/AlSi contact.

For example a distribution layer or RDL can be formed at the surface where the vias emerge, for example by implementing the following steps:

For example, a fine layer 50 of SiN nitride is formed in the rear face, being, for example, of the order of 50 nm thick, together with an RDL installation oxide layer which is several hundreds of nm thick on layer 50.

In a subsequent step a lithography on layer 52 and an etching of RDL oxide 52 take place, stopping at layer 52, so as to form lines 54 etched in the RDL oxide.

In a subsequent step the resin is removed.

Elimination of the SiN in the etched lines 54 perpendicular to the vias then takes place to attain the vias. The lines are then cleaned.

In a subsequent step metallisation of the bottom of the lines takes place, for example with a layer of TiN and copper. This metallisation is, for example, accomplished by PVD over a depth of several hundreds of nm; the lines are then filled with copper 56, deposited for example by ECD, for example over a thickness of 1 μm. Annealing and mechanical-chemical polishing then take place.

Figure 21F:
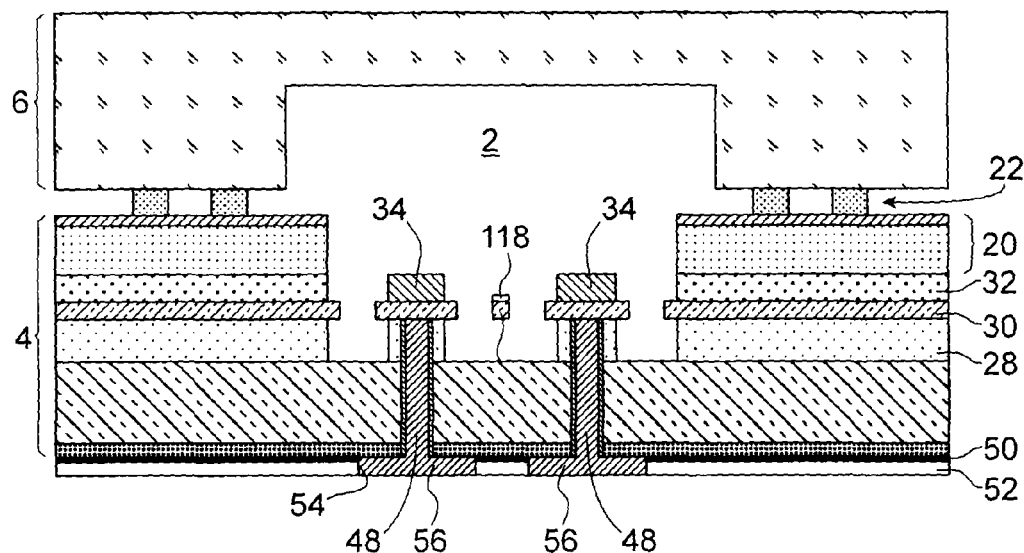

The element obtained in this manner is represented in FIG. 21F.

The RDL layer enables the TSV contacts to be distributed, and the device to be prepared for the connections with the exterior, for example with an integrated circuit. In addition, this layer can enable electrical tests to be accomplished to sort the dies, if required, before assembling them with the integrated circuit, which enables the costs to be optimised while taking account of the productivity aspects, if these are different for the devices of the invention and the integrated circuits.

Alternatively the device can be prepared in a known manner for a connection with integrated circuits (dies or wafers).

By this means operations to connect the devices to integrated circuits can be accomplished by means of operations of the die transfer or wafer transfer type, by connecting the vias of the device of the invention to one of the metal levels of the integrated circuit(s), advantageously through the RDL layer.

This operation can be accomplished in different ways by transferring one wafer to another wafer ("Wafer to Wafer"), or alternatively dies to a wafer ("Die to Wafer") or alternatively dies to dies ("Die to Die"). In the case of a die transfer the dies forming the integrated circuit can be transferred to dies or wafers of devices of the invention, or alternatively vice versa.

The various techniques developed for 3D technologies in particular are conceivable, such as fusible balls, Au—Au sealings, polymer sealings with metal patterns in a damascene configuration, etc.

These techniques can require that preparatory operations are accomplished on the device of the invention and/or on the integrated circuit portion, for example:

by undertaking particular operations to clean the metal layers, for example for direct Cu—Cu sealings by forming an RDL layer, as described above by forming metal patterns (e.g. "Copper Pillar" for a Cu—Cu sealing) at the surface of the device before applying metal-metal sealing techniques such as Cu, Au, etc., sealing techniques with fusible material such as InAu, CuSn, etc.), sealing techniques with eutectic conductors, etc.

by forming fusible beads to apply flip-chip, AuSn, etc. techniques.

In the method which has been described above, an intermediate layer 20 was produced on the substrate comprising the NEMS before sealing to the cap.

But the device according to the invention cannot comprise an intermediate layer. In FIGS. 22A to 22E the steps of production of the vias in a device without an intermediate layer can be seen.

The steps of production of the substrate comprising the NEMS are similar to the steps represented in FIGS. 19A and 19B. In this example there is no production of interconnection lines.

The steps of production of the cap are similar to the steps represented in FIGS. 20A and 20B.

Sealing is accomplished in similar manner to the sealing of the step represented in FIG. 20C. This is preferably a dry film sealing, but alternatively it may be a eutectic sealing, a molecular sealing, a metal sealing by thermocompression, etc.

Production of the vias will now be described.

Production of the vias is similar to that of the steps represented in FIGS. 21C to 21E.

Firstly substrate 4 is thinned in its rear face, for example by grinding followed by CMP, in order to attain a thickness, for example, of between 15 µm and 50 µm.

In a subsequent step a layer 57 of a dielectric material is formed in the rear face.

Figure 22A:
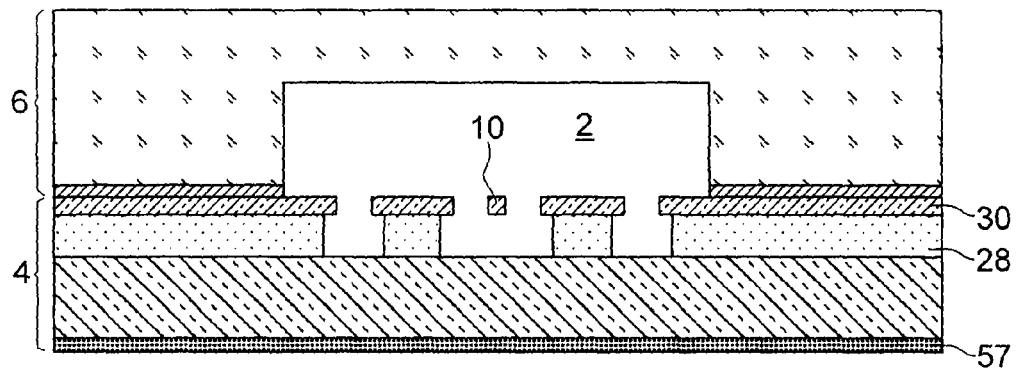

The element obtained in this manner is represented in FIG. 22A.

In a subsequent step holes 58 are etched in the substrate using the method described in relation with FIG. 21C. Etching can stop at NEMS layer 30.

In a subsequent step a layer made of electrically insulating material 60, for example $SiO_2$ SACVD, is deposited on the inner face of the holes, using the method described in relation with FIG. 21D.

Figure 22B:
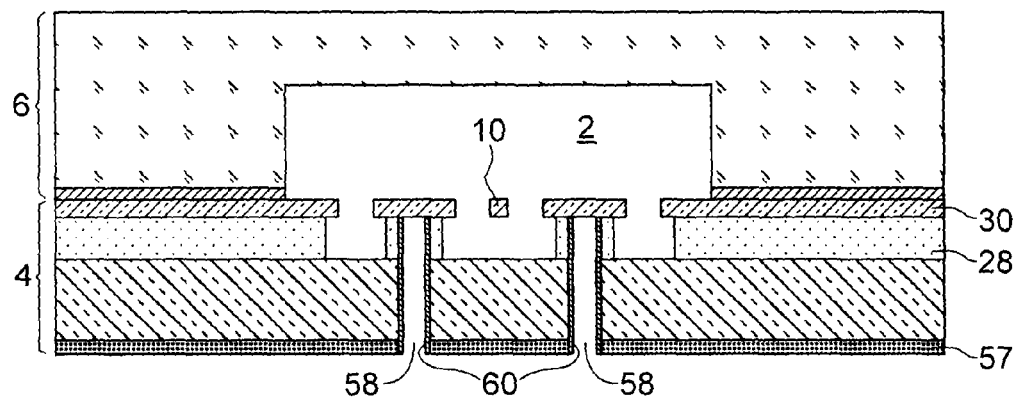

The element obtained in this manner is represented in FIG. 22B.

In a subsequent step the vias are formed by filling the holes with an electrically conductive material 62, preferably a metal, according to the method described in relation with FIG. 21E.

Figure 22C:
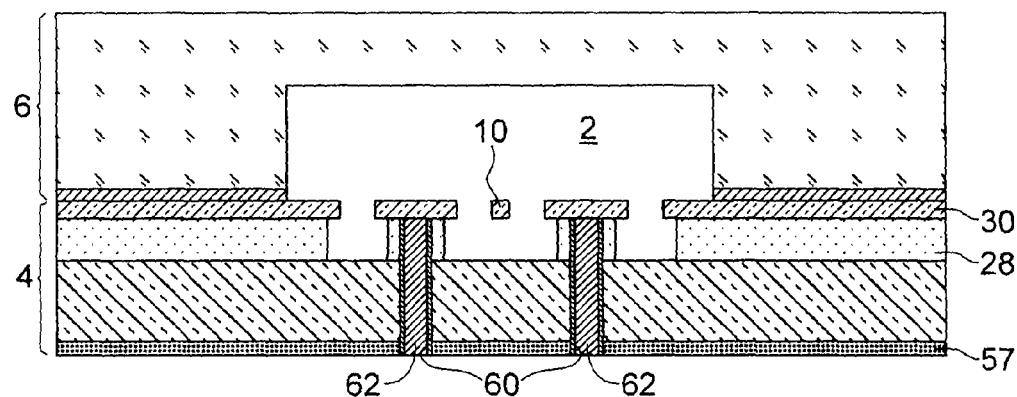

The element obtained in this manner is represented in FIG. 22C.

We shall now describe a method of producing a device comprising an intermediate layer but with no interconnection line in the fluid channel.

The first steps of production of the NEMS substrate are similar to the steps of FIGS. 19A and 19B.

In a subsequent step an intermediate layer 20 is formed on layer 30. It can be formed from several materials, for example it can comprise at the surface a layer which resists the etching to release the NEMS; for example it can be made of amorphous silicon, which resists hydrofluoric acid vapour.

Figure 23A:
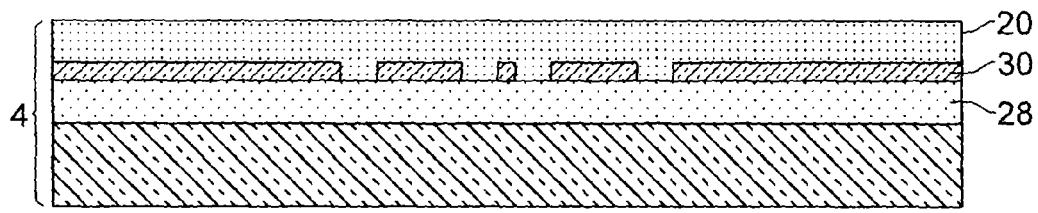
Figure 23B:
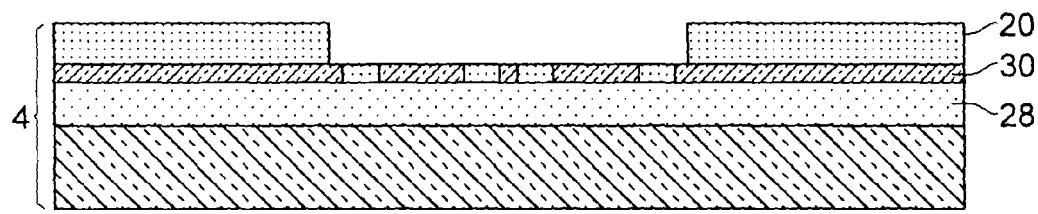

The element obtained in this manner is represented in FIG. 23A.

In a subsequent step intermediate layer 20 is structured so as to provide access to the area where the NEMS structure(s) to be released is/are located. To do so a lithography and an etching of intermediate layer 20 take place. In this example intermediate layer 20 is kept in the assembly area. It could be structured in another way, as was described above, for example only above the sensitive portions, protecting the remainder of the surface, or alternative by etching in the area of the assembly interface to remove the intermediate layer in this area and keep only the fluid channel. The NEMS structure is then released, example using hydrofluoric acid vapour.

Figure 23C:
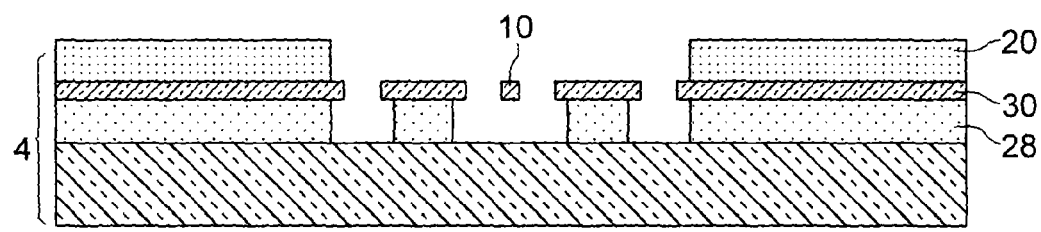

The element obtained in this manner is represented in FIG. 23C.

The steps of production of the cap are similar to the steps represented in FIGS. 20A and 20B.

Sealing is accomplished in similar manner to the sealing of the step represented in FIG. 20C. This is preferably a dry film sealing, but alternatively it may be a eutectic sealing, a molecular sealing, a sealing by thermocompression, etc.

Figure 23D:
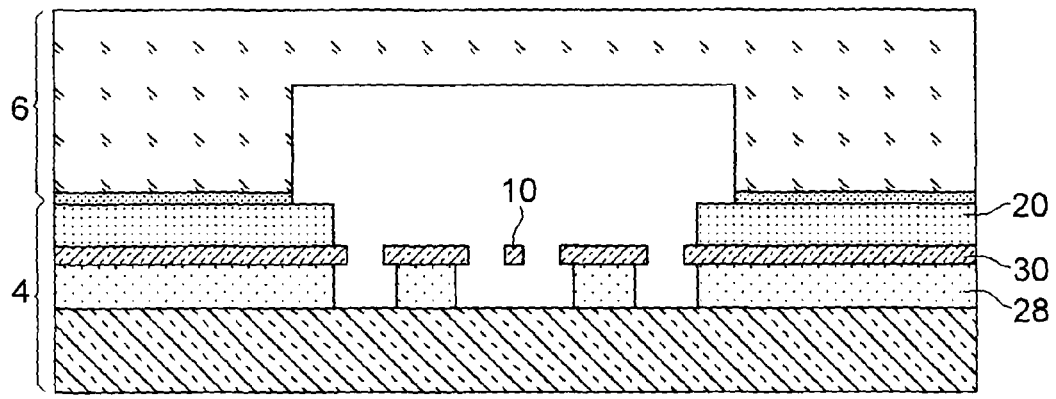
Figure 23E:
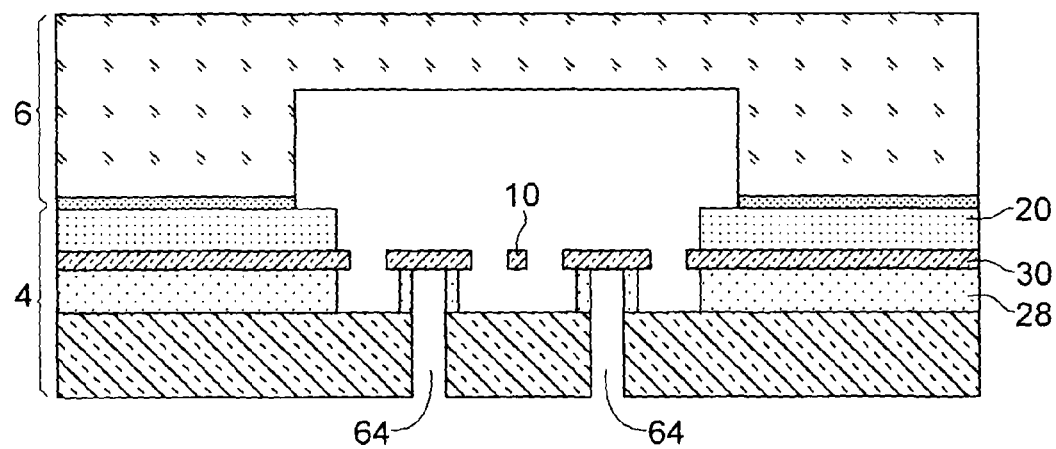

In this embodiment the sealing is made between intermediate layer 20 and cap 6. The element obtained in this manner is represented in FIG. 23D.

Production of the vias will now be described.

Production of the vias is similar to that of the steps represented in FIGS. 21B to 21E.

Firstly substrate 4 is thinned in its rear face, for example by grinding followed by CMP, in order to attain a thickness, for example, of between 15 µm and 50 µm.

In a subsequent step a layer 62 of a dielectric material is formed in the rear face.

In a subsequent step holes 64 are etched in the substrate using the method described in relation with FIG. 21C. The etching can stop at NEMS layer 30 (FIG. 23E), or in sacrificial layer 28.

In a subsequent step a layer made of electrically insulating material 66, for example $SiO_2$ SACVD, is deposited on the inner face of the holes, using the method described in relation with FIG. 21D.

In a subsequent step the vias are formed by filling the holes with an electrically conductive material 38, preferably a metal.

Figure 23F:
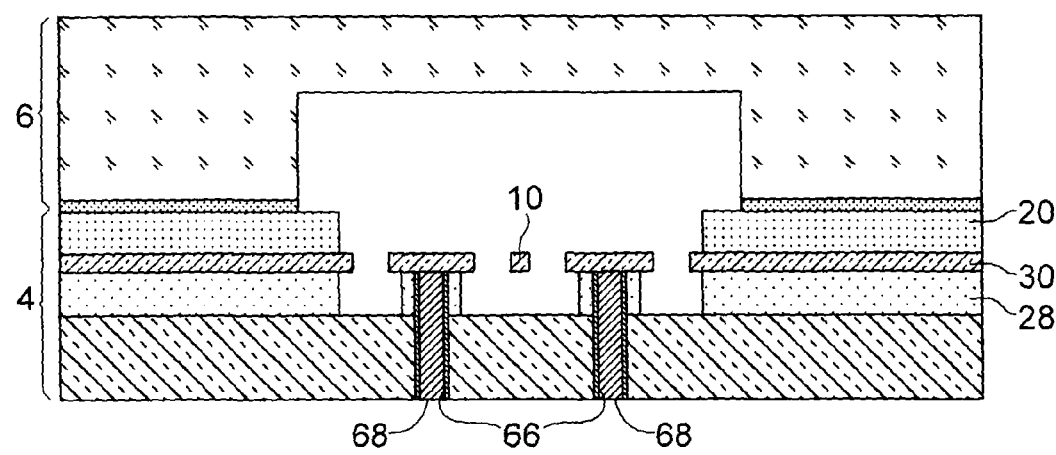

The element obtained in this manner is represented in FIG. 23F.

In the examples of methods described above the vias are produced after the cap is sealed on to the NEMS substrate and after the NEMS are released. But the devices according to the invention could be produced using methods in which the vias would be produced before releasing the NEMS and before sealing the cap on to the NEMS substrate, or after releasing the NEMS and before sealing it between the cap and the NEMS substrate.

As was mentioned above, devices can be manufactured collectively on substrates, for example made of silicon, where the formed assembly comprises several parallel channels. The devices are then separated by cleavage and/or sawing operations, for example. It is desired to divide each channel to form several devices, and to separate the channels from one another.

It is desirable that the fluid channels are not contaminated during the separation steps. To accomplish this, and very advantageously, firstly partial cutting lines are made in the area of the inlets and outlets of the fluid channels, deep within the NEMS substrates and Cap orthogonal to the axis of the fluid channels, but which do not reach these channels, where the cutting lines then define planes perpendicular to the axis of the channel; a cleavage operation then takes place which allows final separation of the devices along the planes defined by the cutting lines.

It should be noted that the planes are secant with the axis of the channel, but are not necessarily perpendicular to this axis.

With regard to separation in the directions parallel to the fluid channels, conventional sawing operations can be used.

Depending on the approaches chosen in the case of a connection of the devices with integrated circuits (WTW, DTW, DTD), the steps of separation of the dies of devices will be able to be undertaken before or after sealing with the integrated circuits.

By virtue of the invention a device can be produced with a fluid channel comprising one or more mechanical structures suspended in the channel, by this means preventing the formation of vias in the cap and/or at the sealing interface and lateral interconnection lines, making production of the tightness between the cap and the NEMS substrate more complex.

In addition, the invention enables networks of mechanical structures to be produced easily, by allowing a dense and complex electrical interconnection as close as possible to the mechanical structures with, possibly, several metal levels. The invention can also enable all the structures and layers present in the channel to be encapsulated, except for the sensitive structures with an encapsulation layer. Finally, it allows functionalisation to be implemented in the course of a method on suspended mechanical structures.

The invention claimed is:

1. A device comprising:
    a substrate comprising at least one electronic structure including at least one of a microelectronic structure and a nanoelectronic structure comprising at least one sensitive portion,
    a cap, said cap being assembled with the substrate at an assembly interface,
    one fluid channel defined between said substrate and said cap, said fluid channel comprising at least two apertures to provide a flow in said channel, said electronic structure being located within the fluid channel,
    at least one electrical connection between said electronic structure and the exterior of the fluid channel, the at least one electrical connection being formed by a via made at least partly through the substrate directly below the electronic structure, and in electrical contact with the electronic structure, and
    an intermediate layer located only at the assembly interface located between the cap and the substrate.

2. A device comprising:
    a substrate comprising at least one electronic structure including at least one of a microelectronic structure and a nanoelectronic structure comprising at least one sensitive portion,
    a cap, said cap being assembled with the substrate at an assembly interface,
    one fluid channel defined between said substrate and said cap, said fluid channel comprising at least two apertures to provide a flow in said channel, said electronic structure being located within the fluid channel,
    at least one electrical connection between said electronic structure and the exterior of the fluid channel, the at least one electrical connection being formed by a via made at least partly through the substrate directly below the electronic structure, and in electrical contact with the electronic structure, and
    an intermediate layer located at least partly in the fluid channel, said intermediate layer covering, in the fluid channel, at least partly the electronic structure, except for the sensitive portion thereof.

3. The device according to claim 2, in which the intermediate layer is an encapsulation layer.

4. The device according to claim 2, in which the via is in electrical contact with the electronic structure through a contact located in the fluid channel.

5. The device according to claim 2, in which the intermediate layer comprises an electrically insulating material.

6. The device according to claim 2, comprising a functionalization layer at least partly covering a part of the sensitive portion of the electronic structure.

7. The device according to claim 2, comprising several microelectronic or nanoelectronic structures interconnected in said fluid channel.

8. The device according to claim 7, in which the microelectronic or nanoelectronic structures are interconnected by interconnection lines positioned in the fluid channel.

9. The device according to claim 8, in which the intermediate layer comprises an electrically insulating material which electrically insulates the interconnection lines.

10. The device according to claim 2, comprising a dry sealing film interposed between the substrate and the cap.

11. The device according to claim 10, in which the dry sealing film comprises several beads.

12. The device according to claim 2, comprising at least one layer of material interposed between the substrate and the cap making a eutectic or metallic sealing, or thermocompression sealing, or screen print sealing, or in which the sealing is a molecular sealing or glass frit.

13. The device according to claim 2, in which the intermediate layer comprises at least a first planarizing layer and a second layer deposited on the first layer, said second layer being made of a material sensitive to a step of release of the electronic structure.

14. The device according to claim 2, in which the channel forms a gas chromatography microcolumn.

15. The device according to claim 2, in which the intermediate layer comprises at least a first planarizing layer and a second layer deposited on the first layer, said second layer being made of a material insensitive to a step of release of the electronic structure.

* * * * *